(12) United States Patent
Kelley et al.

(10) Patent No.: US 7,361,470 B2
(45) Date of Patent: Apr. 22, 2008

(54) ELECTROCATALYTIC NUCLEIC ACID HYBRIDIZATION DETECTION

(75) Inventors: Shana O. Kelley, Boston, MA (US); Melissa Lapierre-Devlin, Somerville, MA (US); Meaghan O'Keefe, Los Angeles, CA (US)

(73) Assignee: Trustees of Boston College, Chestnut Hill, MA (US)

( * ) Notice: Subject to any disclaimer, the term of this patent is extended or adjusted under 35 U.S.C. 154(b) by 0 days.

(21) Appl. No.: 11/270,983

(22) Filed: Nov. 11, 2005

(65) Prior Publication Data

US 2006/0223079 A1 Oct. 5, 2006

Related U.S. Application Data

(63) Continuation of application No. PCT/US04/14788, filed on May 11, 2004.

(60) Provisional application No. 60/470,242, filed on May 13, 2003.

(51) Int. Cl.
C12Q 1/68 (2006.01)
C07H 21/02 (2006.01)
C07H 21/04 (2006.01)

(52) U.S. Cl. .................. 435/6; 536/23.1; 536/24.3

(58) Field of Classification Search .................. 435/6; 536/23.1, 24.3
See application file for complete search history.

(56) References Cited

U.S. PATENT DOCUMENTS

| | | | |
|---|---|---|---|
| 5,312,527 A | 5/1994 | Mikkelsen et al. | |
| 5,972,692 A | 10/1999 | Hashimoto et al. | |
| 6,221,586 B1* | 4/2001 | Barton et al. .................. | 435/6 |
| 6,361,951 B1* | 3/2002 | Thorp et al. .................. | 435/6 |
| 6,479,240 B1* | 11/2002 | Kayyem et al. ............... | 435/6 |
| 2002/0081588 A1* | 6/2002 | De Lumley-woodyear et al. .......................... | 435/6 |
| 2003/0152960 A1* | 8/2003 | Thorp et al. .................. | 435/6 |
| 2005/0084881 A1* | 4/2005 | Kelley et al. .................. | 435/6 |

FOREIGN PATENT DOCUMENTS

| | | |
|---|---|---|
| AU | 758 062 B2 | 3/2003 |
| EP | 0 564 254 A | 10/1993 |
| EP | 1629122 | 3/2006 |
| EP | 1784512 | 5/2007 |
| WO | WO 96/06946 | 3/1996 |
| WO | WO 99/67628 | 12/1999 |
| WO | WO 05/005952 | 10/2005 |
| WO | WO 06/076047 | 7/2006 |
| WO | WO 06/094200 | 9/2006 |
| WO | WO 07/094805 | 8/2007 |

OTHER PUBLICATIONS

Kelley et al. Single-base mismatch detection based on charge transduction through DNA. Nucleic Acids Research 27(24) : 4830-4837 (1999).*
Armistead, P.M. and Thorp, H.H. Electrochemical detection of gene expression in tumor samples: overexpression of Rak nuclear tyrosine kinase. Bioconjug Chem. Mar.-Apr. 2002;13(2):172-6.
Boon, E.M. et al., Mutation detection by electrocatalysis at DNA-modified electrodes. Nat Biotechnol. Oct. 2000;18(10):1096-100. Erratum in: Nat Biotechnol Dec. 2000;18(12):1318.
Brunetti, B et al., Electrochemistry of phenothiazine and methylviologen biosensor electron-transfer mediators at nanoelectrode ensembles. J. Electroanal. Chem. 2000; 491:166-74.
Chilvers, K.F. et al., Phototoxicity of rose bengal in mycological media—implications for laboratory practice. Lett Appl Microbiol. Feb. 1999;28(2);103-7.
Conlon, K.A. et al., Site directed photochemical disruption of the actin cytoskeleton by actin-binding Rose Bengal-conjugates. J Photochem Photobiol B. Nov. 2002;68(2-3):140-6.
Forrer, P. et al., Electrochemical preparation and surface properties of gold nanowire arrays formed by the template technique. J. Appl. Electrochem. 2000; 30:533-41.
Gooding, J.J. et al., Protein electrochemistry using aligned carbon nanotube arrays. J Am Chem Soc. Jul. 30, 2003;125(30):9006-7.
Gore, M.R. et al., Detection of attomole quantities [correction of quantitites] of DNA targets on gold microelectrodes by electrocatalytic nucleobase oxidation. Anal Chem. Dec. 1, 2003;75(23):6586-92.
Hashimoto, K. et al., Novel DNA sensor for electrochemical gene detection. Analytica Chimica Acta. Feb. 18, 1994;286(2):219-224.
Hashimoto, K. et al., Sequence-specific gene detection with a gold electrode modified with DNA probes and an electrochemically active dye. Anal Chem. Nov. 1, 1994;66(21):3830-3.
Lapierre, M.A. et al., Electrocatalytic detection of pathogenic DNA sequences and antibiotic resistance markers. Anal Chem. Nov. 15, 2003;75(22):6327-33.
Liu, S. et al., Voltammetric determination of sequence-specific DNA by electroactive intercalator on graphite electrode. Analytica Chimica Acta. Dec. 20, 1996;335(3):239-243.
Martin, C.R. an Mitchell, D.T. As particle size approaches molecular dimensions, all properties of a material change, making nanomaterials useful for particular applications. Nanomaterials in Anal Chem. May 1, 1998;322A-7A.
Menon, V.P. and Martin, C.R. Fabrication and Evaluation of Nanoelectrode Ensembles. Anal. Chem. 1995; 67:1920-8.
Millan, K.M. and Mikkelsen, S.R. Sequence-selective biosensor for DNA based on electroactive hybridization indicators. Anal Chem. Sep. 1, 1993;65(17):2317-23.
Moretto, L.M. et al., Voltammetry of redox analytes at trace concentrations with nanoelectrode ensembles. Talanta 2004; 62:1055-60.

(Continued)

*Primary Examiner*—Ethan Whisenant
(74) *Attorney, Agent, or Firm*—Wolf, Greenfield & Sacks P.C.

(57) ABSTRACT

The detection of specific DNA sequences using electro-chemical readout would permit the rapid and inexpensive detection and identification of bacterial pathogens and the analysis of human genes. A new assay developed for this purpose is described that harnesses an electrocatalytic process to monitor DNA hybridization.

20 Claims, 12 Drawing Sheets

OTHER PUBLICATIONS

Napier, M.E. et al., Probing biomolecule recognition with electron transfer: electrochemical sensors for DNA hybridization. Bioconjug Chem. Nov.-Dec. 1997;8(6):906-13.

Palecek, E. et al., Electrochemical biosensors for DNA hybridization and DNA damage. Biosens Bioelectron. Sep. 15, 1998;13(6):621-8.

Patolsky, F. et al., Electronic Transduction of Polymerase or Reverse Transcriptase Induced Replication Processes on Surfaces: Highly Sensitive and Specific Detection of Viral Genomes Angew Chem Int Ed Engl. Jun. 18, 2001;40(12):2261-5.

Ropp, P.A. and Thorp, H.H. Site-selective electron transfer from purines to electrocatalysts: voltammetric detection of a biologically relevant deletion in hybridized DNA duplexes. Chem Biol. Sep. 1999;6(9):599-605.

Steel, A. B. et al., Electrochemical quantitation of DNA immobilized on gold. Anal Chem. Nov. 15, 1998;70(22):4670-7.

Taft, B.J. et al., Engineering DNA-electrode connectivities: manipulation of linker length and structure. Analytica Chimica Acta. Oct. 31, 2003;496(1-2):81-91.

Thorp, H.H. Cutting out the middleman: DNA biosensors based on electrochemical oxidation. Trends in Biotechnology. 1998;16:117-121.

Vercoutere, W. and Akeson, M. Biosensors for DNA sequence detection. Curr Opin Chem Biol. Dec. 2002;6(6):816-22. Review.

Wang, J. From DNA biosenors to gene chips. Nucleic Acids Res. Aug. 15, 2000;28(16):3011-6. Review.

Xu, X.-H. et al., Immobilization of DNA on an Aluminum(III) Alkanebisphosphonate Thin Film with Electrogenerated Chemiluminescent Detection. J. Am. Chem. Soc. 1994; 116(18):8386-7.

Yu, S. et al. Nano Wheat Fields Prepared by Plasma-Etching Gold Nanowire-Containing Membranes. Nano Lett. 2004;3:815-8.

Coche-Guerente et al., Amplification of amperometric biosensor responses by electrochemical substrate recycling. 3. Theoretical and experimental study of the phenol-polyphenol oxidase system immobilized in Laponite hydrogels and layer-by-layer self-assembled structures. Anal Chem. 2001 Jul. 15;73(14):3206-18.

* cited by examiner

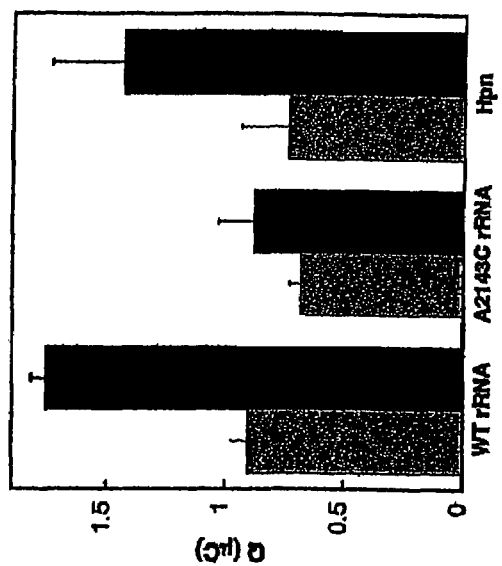
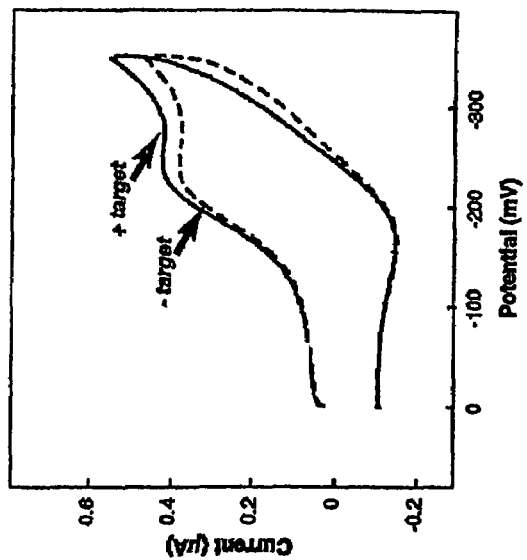
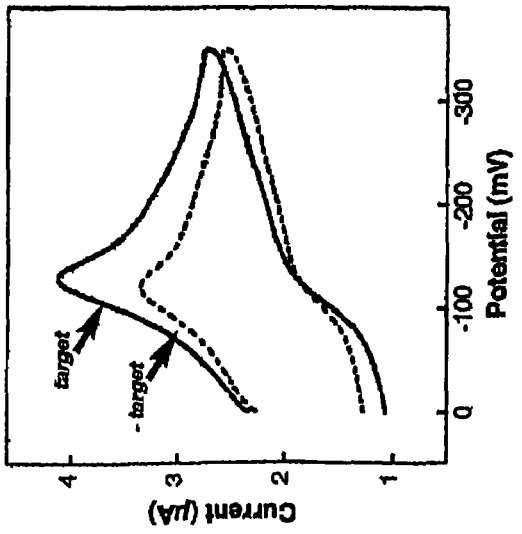
Fig. 5A
Fig. 5B
Fig. 5C

SEQUENCE LISTING

```
<160> NUMBER OF SEQ ID NOS: 17

<210> SEQ ID NO 1
<211> LENGTH: 30
<212> TYPE: DNA
<213> ORGANISM: Artificial sequence
<220> FEATURE:
<223> OTHER INFORMATION: T1 (hpn target)

<400> SEQUENCE: 1
tgttgcagca ctagcgatag tcatcatcaa                              30

<210> SEQ ID NO 2
<211> LENGTH: 18
<212> TYPE: DNA
<213> ORGANISM: Artificial sequence
<220> FEATURE:
<223> OTHER INFORMATION: T2a (WT rRNA target)

<400> SEQUENCE: 2
ggcaagacgg aaagaccc                                           18

<210> SEQ ID NO 3
<211> LENGTH: 18
<212> TYPE: DNA
<213> ORGANISM: Artificial sequence
<220> FEATURE:
<223> OTHER INFORMATION: T2aMUT (A2143C rRNA target)

<400> SEQUENCE: 3
ggcaagacgg acagaccc                                           18
```

<210> SEQ ID NO 4
<211> LENGTH: 30
<212> TYPE: DNA
<213> ORGANISM: Artificial sequence
<220> FEATURE:
<223> OTHER INFORMATION: HP1b (18 nt + 12T complementary hpn probe)

<400> SEQUENCE: 4
tttttttttt ttgatgacta tcgctagtgc                                    30

<210> SEQ ID NO 5
<211> LENGTH: 30
<212> TYPE: DNA
<213> ORGANISM: Artificial sequence
<220> FEATURE:
<223> OTHER INFORMATION: HP1c (18 nt + 12T noncomplementary hpn probe)

<400> SEQUENCE: 5
tttttttttt ttgggataat tcttcaccgg                                    30

<210> SEQ ID NO 6
<211> LENGTH: 219
<212> TYPE: DNA
<213> ORGANISM: Artificial sequence
<220> FEATURE:
<223> OTHER INFORMATION: Target sequence (PCR product)

<400> SEQUENCE: 6
ggagtcatca tggcacacca tgaagaacag cacggcggtc atcaccacca tcaccaccac    60
acacaccacc accactatca cggcggtgaa caccaccatc accaccacag ctctcatcat   120
gaagaaggtt gttgcagcac tagcgatagt catcatcatc aagaagaggg ttgctgccac   180
gggcatcacg agtaatatcg gtgtggctag gggcaactt                          219

<210> SEQ ID NO 7
<211> LENGTH: 225
<212> TYPE: DNA
<213> ORGANISM: Artificial sequence
<220> FEATURE:
<223> OTHER INFORMATION: Target sequence (RNA transcript)

<400> SEQUENCE: 7
atcaaaggag tcatcatggc acaccatgaa gaacagcacg gcggtcatca ccaccatcac    60
caccacacac accaccacca ctatcacggc ggtgaacacc accatcacca ccacagctct   120
catcatgaag aaggttgttg cagcactagc gatagtcatc atcatcaaga gagggttgc   180 tgccacgggc atcacgagta atatcggtgt ggctaggggc aactt                   225

<210> SEQ ID NO 8
<211> LENGTH: 33
<212> TYPE: DNA
<213> ORGANISM: Artificial sequence
<220> FEATURE:
<223> OTHER INFORMATION: 30-mer oligonucleotide for Hpn target detection

<400> SEQUENCE: 8
tgttgcagca ctagcgatag tcatcatcat caa                                33

<210> SEQ ID NO 9
<211> LENGTH: 24
<212> TYPE: DNA
<213> ORGANISM: Artificial sequence
<220> FEATURE:
<223> OTHER INFORMATION: Forward PCR primer for H. pylori hpn gene
      amplification

```
<400> SEQUENCE: 9
atcaaaggag tcatcatggc acac                                              24

<210> SEQ ID NO 10
<211> LENGTH: 18
<212> TYPE: DNA
<213> ORGANISM: Artificial sequence
<220> FEATURE:
<223> OTHER INFORMATION: Reverse PCR primer for H. pylori hpn gene
      amplification

<400> SEQUENCE: 10
aagttgcccc tagccaca                                                     18

<210> SEQ ID NO 11
<211> LENGTH: 41
<212> TYPE: DNA
<213> ORGANISM: Artificial sequence
<220> FEATURE:
<223> OTHER INFORMATION: Forward PCR primer containing the T7 polymerase
      promoter sequence

<400> SEQUENCE: 11
gctaggtaat acgactcact ataggagtca tcatggcaca c                           41

<210> SEQ ID NO 12
<211> LENGTH: 30
<212> TYPE: DNA
<213> ORGANISM: Artificial sequence
<220> FEATURE:
<223> OTHER INFORMATION: HP1a (30 nt complementary hpn probe):

<400> SEQUENCE: 12
ttgatgatga ctatcgctag tgctgcaaca                                        30

<210> SEQ ID NO 13
<211> LENGTH: 18
<212> TYPE: DNA
<213> ORGANISM: Artificial sequence
<220> FEATURE:
<223> OTHER INFORMATION: HP2a (rRNA probe)

<400> SEQUENCE: 13
gggtctttcc gtcttgcc                                                     18

<210> SEQ ID NO 14
<211> LENGTH: 18
<212> TYPE: DNA
<213> ORGANISM: Artificial sequence
<220> FEATURE:
<223> OTHER INFORMATION: HP2b (rRNA probe-2)

<400> SEQUENCE: 14
ggtccacggg gtctttcc                                                     18

<210> SEQ ID NO 15
<211> LENGTH: 18
<212> TYPE: DNA
<213> ORGANISM: Artificial sequence
<220> FEATURE:
<223> OTHER INFORMATION: T2b (WT rRNA target #2)

<400> SEQUENCE: 15
ggaaagaccc cgtggacc                                                     18
```

```
<210> SEQ ID NO 16
<211> LENGTH: 18
<212> TYPE: DNA
<213> ORGANISM: Artificial sequence
<220> FEATURE:
<223> OTHER INFORMATION: T2bMUT (A2143C rRNA target #2)

<400> SEQUENCE: 16
ggacagaccc cgtggacc                                                18

<210> SEQ ID NO 17
<211> LENGTH: 15
<212> TYPE: DNA
<213> ORGANISM: Artificial sequence
<220> FEATURE:
<223> OTHER INFORMATION: T-NC (noncomplementary target)

<400> SEQUENCE: 17
aacagttcct gcatg                                                   15
```

ELECTROCATALYTIC NUCLEIC ACID HYBRIDIZATION DETECTION

RELATED APPLICATIONS

This application is a continuation of PCT/US2004/014788, filed on May 11, 2004, which claims priority to U.S. Provisional Application No. 60/470,242, filed on May 13, 2003, the entirety of which are hereby incorporated by reference in their entirety

GOVERNMENT SUPPORT

The invention was supported, in whole or in part, by Grant No. R21CA097945 by the National Institutes of Health. The Government has certain rights in the invention.

BACKGROUND

The application of newly available genetic information to advances in preventative medicine and disease treatment requires efficient and accurate DNA detection technologies.[1,2] One focus of recent technological developments is systems that exploit differential DNA hybridization at solid surfaces.[3-6] In theory, hybridization of target sequences representing microbial genomic fragments or human disease-related genes to immobilized probe sequences would permit high-sensitivity and high-throughput DNA detection. Moreover, if closely related sequences could be discriminated, microbial pathogens could be detected and identified.

A variety of spectroscopic and analytical techniques can be used to detect DNA hybridization at surfaces.[7-22] DNA-modified gold nanoparticles can be used to detect DNA sequences using optical and fluorescence spectroscopy.[12,18] Surface plasmon resonance also provides a means to monitor hybridization of target sequences to DNA-modified gold substrates in real time.[3,4,19,20,22] The results obtained with these methods indicate that high-sensitivity DNA detection can be achieved when immobilized oligonucleotides are used to capture sequences from solution.

Other gene detection methods (e.g., U.S. Pat. No. 5,972,692, and U.S. Pat. No. 5,312,527) do not use an electrocatalytic assay for DNA hybridization detection.

The detection of DNA sequences using electrochemical readout is particularly attractive for the development of clinical diagnostics.[2,6,23,24] Quantitative electrochemical measurements of this type can be made using compact and inexpensive instrumentation, and covalently labeling DNA samples with reporter groups is typically unnecessary, simplifying sample preparation procedures. Indeed, a number of methods have been reported for the electrochemical detection of DNA, most of which rely on the signal produced by a noncovalently bound redox-active reporter group that is increased when DNA is hybridized to a surface modified with a probe sequence.[7-11,13,15,21] In addition, single-base substitutions producing base mismatches within DNA duplexes immobilized on gold surfaces can be detected electrochemically using intercalating probes.[14,16] The interruption of base stacking caused by the mismatch attenuates the current flowing to the reporter by interfering with DNA-mediated electronic coupling. This effect would potentially permit the electrochemical detection of disease-related point mutations.

Electrocatalytic processes that amplify the signals obtained at DNA-modified electrode surfaces provide a powerful means to increase the sensitivity and accuracy of a detection assay. Electrochemically-generated $Ru(bpy)_3^{3+}$ reacts with guanines contained within a hybridized target in a catalytic process that generates large signals that can be used to detect DNA hybridization, albeit with limitations because of sequence dependence.[13,15,21,24] In addition, an electrocatalytic reaction between an intercalating probe, methylene blue, and solution-borne $Fe(CN)_6^{3-}$ has been used to amplify the signal changes reporting the presence of mismatch-producing point mutations.[16] However, neither system is ideal for hybridization-based detection of closely related sequences.

SUMMARY

The invention relates to a new electrocatalytic nucleic acid detection assay that reports nucleic acid hybridization between a nucleic acid probe and a nucleic acid, or between a first nucleic acid and a second nucleic acid, and can resolve single-base changes in a target nucleic acid sequence. The method exploits a reaction between a redox pair comprising a first redox-active probe (i.e., a nucleic acid-binding compound) and a second redox-active probe. The nucleic acid-binding compound (the first redox-active probe) comprises a redox active compound that can bind to the nucleic acid electrostatically and can be reduced at low potential. This compound is bound to the nucleic acid, producing an electrostatically bound complex. The signal generated by the binding can be amplified by use of a redox active probe that can reoxidize the electrostatically bound complex.

The nucleic acid-binding compound can be a transition metal complex. Preferably, the transition metal is one selected from the group consisting of cobalt, iron, molybdenum, osmium, ruthenium and rhenium. Also preferably, the transition metal complex is an ammonium complex of the transition metal. More preferably, the transition metal complex is $Ru(NH_3)_6^{3+}$. The redox active probe can also be a transition metal complex. Preferably, the transition metal is one selected from the group consisting of cobalt, molybdenum, osmium, iron and rhenium. Also preferably, the transition metal complex is a cynate complex of the transition metal. More preferably, the transition metal complex is $Fe(CN)_6^{-3}$.

The nucleic acid-binding compound binds to the nucleic acid primarily through electrostatic interactions with the phosphate backbone, and therefore its electrochemical reduction yields a signal that reports on the increase of negatively charged groups at the electrode surface upon hybridization of a target nucleic acid. The signal is amplified by the transition metal oxidant of the redox active probe which permits the transition metal to be regenerated for multiple cycles. The immobilization of the nucleic acid probe on highly conductive surfaces, e.g., gold, amplifies the kinetic effects of base mismatches on nucleic acid hybridization, permitting single-base changes to be resolved.

The assay of the present invention can be used to detect genes from pathogens, such as bacteria or viruses, or can be used to detect the expression of genes in a subject.

Preferably, the method is used to detect hybridization between two nucleic acid molecules. The invention also includes a method for detecting hybridization between two DNA or RNA molecules, or between DNA and RNA molecules.

The invention features a method of detecting nucleic acid hybridization between a nucleic acid probe and a target nucleic acid in a sample, where the method includes the steps of: (a) providing a nucleic acid probe immobilized on a solid substrate; (b) contacting, under hybridizing conditions, the solid support and the immobilized probe to a solution containing the sample and a redox pair, wherein the redox pair comprises a first transition metal complex and a second transition metal complex; and (c) measuring the electrocatalytic signal generated by hybridization of the nucleic acid probe and the target nucleic acid; where an increase of the signal detected in step (c) relative to that of a control sample containing no nucleic acid, indicates that the nucleic acid hybridization has occurred. The method can also include an additional step of testing a control, by contacting, under hybridizing conditions, the solid support and the immobilized nucleic acid probe to a solution containing no sample, and a redox pair comprising a first transition metal complex and a second transition metal complex.

Preferably, the transition metal of the first transition metal complex is one selected from the group consisting of cobalt, iron, molybdenum, osmium, ruthenium and rhenium. More preferably, the transition metal of the first transition metal complex is ruthenium. Also preferably, the first transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

Preferably, the transition metal of the second transition metal complex is one selected from the group consisting of cobalt, molybdenum, osmium and rhenium. More preferably, the transition metal of the second transition metal complex is iron. Also preferably, the second transition metal complex is a transition metal cynate complex. More preferably, the second transition metal cynate complex comprises a transition metal selected from the group consisting of cobalt, molybdenum, osmium and rhenium. Most preferably, the second transition metal cynate complex is $Fe(CN)_6^{-3}$.

The invention also features a method of detecting nucleic acid hybridization between a first nucleic acid and a second nucleic acid, wherein the method includes the steps of: (a) providing the first nucleic acid immobilized on a solid support; (b) contacting, under hybridizing conditions, the solid support and the immobilized first nucleic acid to a solution suspected of containing the second nucleic acid and a redox pair comprising a first transition metal complex and a second transition metal complex; and (c) measuring the electrocatalytic signal generated by hybridization of the first and second nucleic acids; wherein an increase of the signal detected in step (c) relative to that of an unhybridized first nucleic acid, indicates that nucleic acid hybridization has occurred. The method can also include an additional step of testing a control, by contacting, under hybridizing conditions, the solid support and the immobilized first nucleic acid to a solution containing no sample, and a redox pair comprising a first transition metal complex and a second transition metal complex.

Preferably, the transition metal of the first transition metal complex is one selected from the group consisting of cobalt, iron, molybdenum, osmium, ruthenium and rhenium. More preferably, the transition metal of the first transition metal complex is ruthenium. Also preferably, the first transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

Preferably, the transition metal of the second transition metal complex is one selected from the group consisting of cobalt, molybdenum, osmium and rhenium. More preferably, the transition metal of the second transition metal complex is iron. Also preferably, the second transition metal complex is a transition metal cynate complex. More preferably, the second transition metal cynate complex comprises a transition metal selected from the group consisting of cobalt, molybdenum, osmium and rhenium. Most preferably, the second transition metal cynate complex is $Fe(CN)_6^{-3}$.

In another aspect, the invention features a method of detecting a mismatch between a first nucleic acid and a second nucleic acid, comprising: (a) providing a nucleic acid probe immobilized on a solid support; (b) contacting, under hybridizing conditions, the solid support and the immobilized probe to a solution containing the sample containing a target nucleic acid and a redox pair, wherein the redox pair comprises a first transition metal complex and a second transition metal complex; and (c) measuring the electrocatalytic signal generated by hybridization of the nucleic acid probe and the target nucleic acid; wherein a decrease of the signal detected in step (c) relative to that of a perfect complementarity between the nucleic acid probe and the target nucleic acid, indicates that there is a mismatch between the first nucleic acid and the second nucleic acid. The method can also include an additional step of testing a control, by contacting, under hybridizing conditions, the solid support and the immobilized nucleic acid probe to a solution containing no sample, and a redox pair comprising a first transition metal complex and a second transition metal complex.

Preferably, the transition metal of the first transition metal complex is one selected from the group consisting of cobalt, iron, molybdenum, osmium, ruthenium and rhenium. More preferably, the transition metal of the first transition metal complex is ruthenium. Also preferably, the first transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

Preferably, the transition metal of the second transition metal complex is one selected from the group consisting of cobalt, molybdenum, osmium and rhenium. More preferably, the transition metal of the second transition metal complex is iron. Also preferably, the second transition metal complex is a transition metal cynate complex. More preferably, the second transition metal cynate complex comprises a transition metal selected from the group consisting of cobalt, molybdenum, osmium and rhenium. Most preferably, the second transition metal cynate complex is $Fe(CN)_6^{-3}$.

The invention additionally features a method of detecting a mismatch between a first nucleic acid and a second nucleic acid, wherein the method includes the following steps: (a) providing the first nucleic acid immobilized on a solid support; (b) contacting, under hybridizing conditions, the solid support and the immobilized first nucleic acid to a solution containing the sample containing the second nucleic acid and a redox pair, wherein the redox pair comprises a first transition metal complex and a second transition metal complex; and (c) measuring the electrocatalytic signal generated by hybridization of the first nucleic acid and the second nucleic acid; wherein a decrease of the signal detected in step (c) relative to that of a perfect complementarity between the first nucleic acid and the second nucleic acid, indicates that there is a mismatch between the first nucleic acid and the second nucleic acid. The method can also include an additional step of testing a control, by contacting, under hybridizing conditions, the solid support and the immobilized nucleic acid probe to a solution containing no sample, and a redox pair comprising a first transition metal complex and a second transition metal complex.

Preferably, the transition metal of the first transition metal complex is one selected from the group consisting of cobalt, iron, molybdenum, osmium, ruthenium and rhenium. More preferably, the transition metal of the first transition metal complex is ruthenium. Also preferably, the first transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

Preferably, the transition metal of the second transition metal complex is one selected from the group consisting of cobalt, molybdenum, osmium and rhenium. More preferably, the transition metal of the second transition metal complex is iron. Also preferably, the second transition metal complex is a transition metal cynate complex. More preferably, the second transition metal cynate complex comprises a transition metal selected from the group consisting of cobalt, molybdenum, osmium and rhenium. Most preferably, the second transition metal cynate complex is $Fe(CN)_6^{-3}$.

The invention also features a method of detecting nucleic acid hybridization between a nucleic acid probe and a target nucleic acid, where the method includes the following steps: (a) providing a nucleic acid probe immobilized on a solid support; (b) contacting the immobilized probe to a solution containing: (i) a transition metal complex; (c) measuring the electrocatalytic signal generated; (d) contacting the immobilized probe to a solution containing: (i) a sample thought to include the target nucleic acid, and (ii) a transition metal complex; (e) measuring the electrocatalytic signal generated; wherein an increase in the signal detected in step (e) over the signal generated in step (c) indicates that hybridization between the nucleic acid probe and the target nucleic acid has occurred. Preferably, the transition metal of the transition metal complex is one selected from the group consisting of cobalt, iron, molybdenum, osmium, ruthenium and rhenium. More preferably, the transition metal of the transition metal complex is ruthenium. Also preferably, the transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

The solutions can also include a second transition metal complex to enhance the electrocatalytic signal generated. Preferably, the transition metal of the second transition metal complex is one selected from the group consisting of cobalt, molybdenum, osmium and rhenium. More preferably, the transition metal of the second transition metal complex is iron. Also preferably, the second transition metal complex is a transition metal cynate complex. More preferably, the second transition metal cynate complex comprises a transition metal selected from the group consisting of cobalt, molybdenum, osmium and rhenium. Most preferably, the second transition metal cynate complex is $Fe(CN)_6^{-3}$.

The method can also include rinsing steps, e.g., rinsing the electrode between contact with the different solutions.

The invention additionally features a method of detecting the presence of a target nucleic acid in a sample, wherein the method includes the following steps: (a) providing a nucleic acid probe immobilized on a solid support; (b) contacting the immobilized probe to a solution containing: (i) a transition metal complex; (c) measuring the electrocatalytic signal generated; (d) contacting the immobilized probe to a solution containing: (i) a sample thought to include the target nucleic acid, and (ii) a transition metal complex; (e) measuring the electrocatalytic signal generated; wherein an increase in the signal detected in step (e) over the signal generated in step (c) indicates the target nucleic acid is present in the sample. Preferably, the transition metal of the transition metal complex is one selected from the group consisting of cobalt, iron, molybdenum, osmium, ruthenium and rhenium. More preferably, the transition metal of the transition metal complex is ruthenium. Also preferably, the transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

The solutions can also include a second transition metal complex to enhance the electrocatalytic signal generated. Preferably, the transition metal of the second transition metal complex is one selected from the group consisting of cobalt, molybdenum, osmium and rhenium. More preferably, the transition metal of the second transition metal complex is iron. Also preferably, the second transition metal complex is a transition metal cynate complex. More preferably, the second transition metal cynate complex comprises a transition metal selected from the group consisting of cobalt, molybdenum, osmium and rhenium. Most preferably, the second transition metal cynate complex is $Fe(CN)_6^{-3}$.

The method can also include rinsing steps, e.g., rinsing the electrode between contact with the different solutions.

The invention further features a method of detecting a mismatch between two nucleic acids, where the method includes the following steps: (a) providing a nucleic acid probe immobilized on a solid support; (b) contacting the immobilized probe to a solution containing: (i) a transition metal complex; (c) measuring the electrocatalytic signal generated; (d) contacting the immobilized probe to a solution containing: (i) a sample thought to include the target nucleic acid, and (ii) a transition metal complex; (e) measuring the electrocatalytic signal generated; wherein a decrease in the signal detected in step (e) over the signal generated in step (c) indicates that there is a mismatch between the nucleic acid probe and the target nucleic acid. Preferably, the transition metal of the transition metal complex is one selected from the group consisting of cobalt, iron, molybdenum, osmium, ruthenium and rhenium. More preferably, the transition metal of the transition metal complex is ruthenium. Also preferably, the transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

The solutions can also include a second transition metal complex to enhance the electrocatalytic signal generated. Preferably, the transition metal of the second transition metal complex is one selected from the group consisting of cobalt, molybdenum, osmium and rhenium. More preferably, the transition metal of the second transition metal complex is iron. Also preferably, the second transition metal complex is a transition metal cynate complex. More preferably, the second transition metal cynate complex comprises a transition metal selected from the group consisting of cobalt, molybdenum, osmium and rhenium. Most preferably, the second transition metal cynate complex is $Fe(CN)_6^{-3}$.

The method can also include rinsing steps, e.g., rinsing the electrode between contact with the different solutions.

In any of the methods described herein, the solid support can be a gold electrode.

The invention also includes a kit for carrying out the method, including a nucleic acid probe immobilized on a conducting electrode, and redox reagents. The kit can include positive control samples that include target nucleic acids, and negative control samples that contain no target nucleic acid. The kit can also include specific types of positive controls, e.g., target nucleic acids that are characteristic of specific target pathogens and genes. The kit can also include packaging materials and instructions for use.

BRIEF DESCRIPTION OF THE DRAWINGS

FIG. 2A: without target. FIG. 2B: with target.

FIGS. 5A, 5B and 5C are a pair of voltammograms and a bar graph. FIG. 5A is a cyclic voltammogram illustrating enhancement of the electrocatalytic signal upon hybridization of target sequence. The initial signal is shown as a dotted trace, and the signal obtained after introduction of the target is shown as a solid line. FIG. 5B is a voltammogram obtained with the same electrodes but in the presence of Ru(III) only, which displays a very small signal increase upon introduction of the target. FIG. 5C shows detection of *H. pylori*-related sequences by monitoring integrated charge. Data displayed correspond to change in charge after 30 minutes of hybridization.

DETAILED DESCRIPTION

Figure 1:
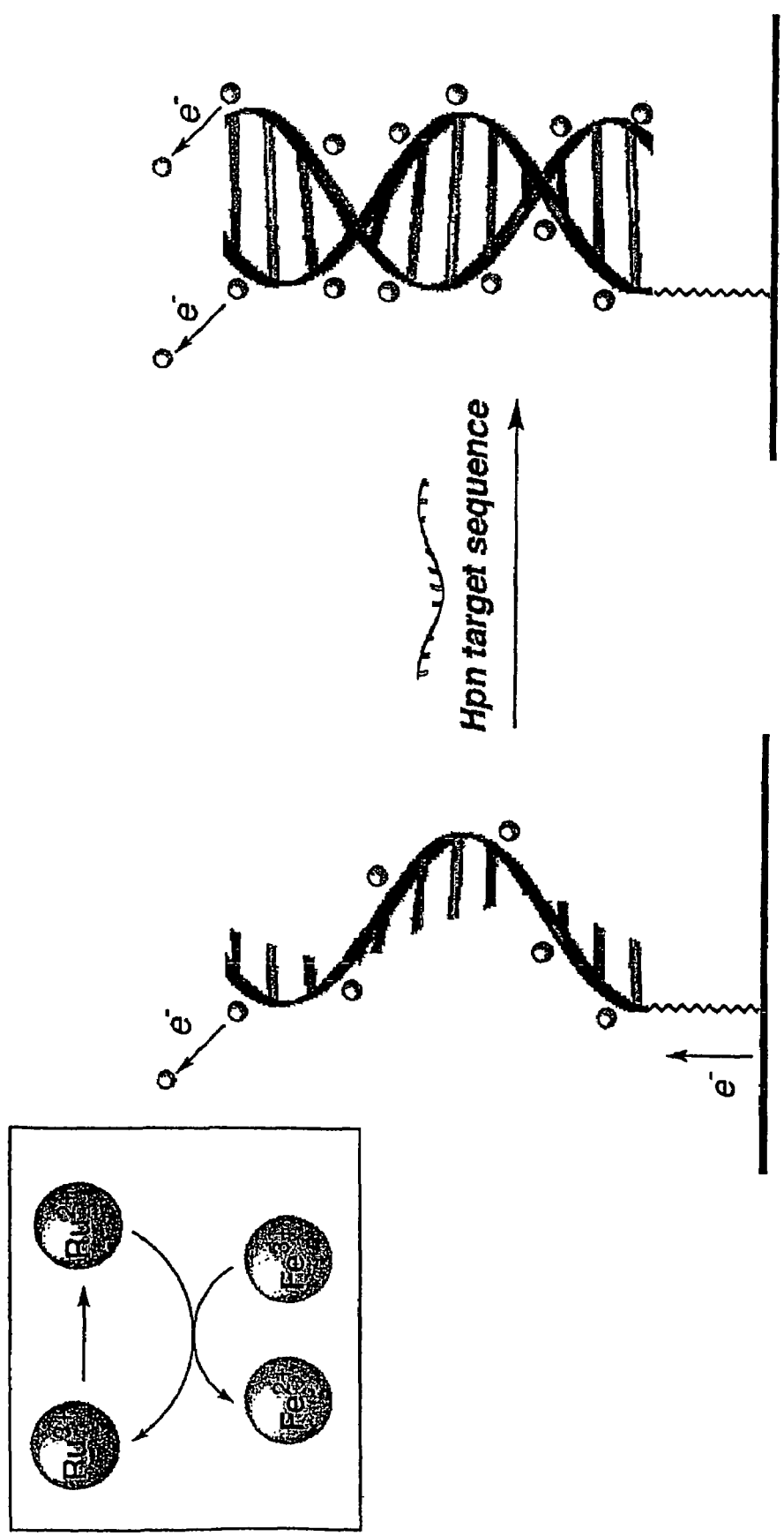
FIG. 1 is an illustration of electrocatalytic detection of DNA hybridization of an *H. pylori* sequence.

The invention relates to a new electrocatalytic nucleic acid detection assay that reports nucleic acid hybridization between a nucleic acid probe and a nucleic acid, or between a first nucleic acid and a second nucleic acid, and can resolve single-base changes in a target nucleic acid sequence. The method exploits a reaction between a redox pair comprising a first redox-active probe (i.e., a nucleic acid-binding compound) and a second redox-active probe. The nucleic acid-binding compound comprises a redox active compound that can bind to the nucleic acid electrostatically and can be reduced at low potential. This compound is bound to the nucleic acid, producing an electrostatically bound complex. The signal generated by the binding can be amplified by use of a redox active probe that can reoxidize the electrostatically bound complex.

DEFINITIONS

"Solid support", as used herein, refers to the material to which the nucleic acid probe is attached. Suitable solid supports are available commercially, and will be apparent to the skilled person. The supports can be manufactured from materials such as glass, ceramics, silica and silicon, and can incorporate conductive material to serve as an electrode. Conductive supports with a gold surface may also be used. The supports usually comprise a flat (planar) surface, or at least a structure in which the polynucleotides to be interrogated are in approximately the same plane. The support can be an electrode, or can be attached to an electrode.

"Mismatch", as used herein, refers to a duplex in which less than all of the nucleotides on one strand are perfectly matched to the other strand (e.g., where nucleotide pairing other than adenosine-thymine or guanine-cytosine occurs, e.g., nucleotide paring such as adenosine-cytosine, adenosine-guanine, adenosine-adenosine, thymine-cytosine, thymine-guanine, thymine-thymine, guanine-guanine, or cytosine-cytosine occurs), where a deletion or insertion of one or more DNA nucleotides on one strand as compared to the other complementary strand occurs (e.g., a deletion of 1, 2, 5, 10, 15, or more nucleotides or an insertion of 1, 2, 5, 10, 15, or more nucleotides occurs), or other mismatches between the two strand of the duplex occurs. DNA mismatches may arise from nucleic acid replication errors, mutagenesis, deamination of 5-methylcytosine, formation of thymidine dimers, nucleic acid recombination, etc.

By "probe" is meant a single-stranded oligonucleotide capable of binding to at least a portion of the target nucleic acid sought to be detected. The probe will generally have a sequence partly or completely complementary to a target nucleic acid sequence sought to be detected, so as to stably hybridize thereto under stringent hybridization conditions. In the case of a group or species-specific probe, the probe has the ability to stably hybridize to a target nucleic acid and not to non-target nucleic acids such as those from organisms outside the phylogenetic group or species under stringent hybridization conditions. Probes may, but need not, have regions which are not complementary to a target sequence, as long as such sequences do not substantially alter the probe's desired specificity under stringent hybridization conditions.

As used herein, the term "a nucleic acid probe" also refers to a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified on bases (7-deazaguanosine, inosine, etc.) or on sugar moiety. In addition, the bases in a probe can be joined by a linkage other than a phosphodiester bond, so long as it does not interfere with hybridization. Thus, for example, probes can be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. By assaying for the presence or absence of the probe, one can detect the presence or absence of the select sequence or subsequence.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs and, as applicable to the embodiment being described, single (sense or antisense) and double-stranded polynucleotides. ESTs, chromosomes, cDNAs, mRNAs, and rRNAs are representative examples of molecules that can be referred to as nucleic acids.

As used herein, the term "hybridization" refers to any process by which a strand of nucleic acid binds with a complementary strand through base pairing.

As used herein, the term "hybridization conditions" refer to standard conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety. Non-limiting examples of hybridization conditions include low stringency hybridization conditions, moderate stringency hybridization conditions and high stringency hybridization conditions.

As used herein, the term "sample" as used in its broadest sense, refers to any plant, animal or viral material containing DNA or RNA, such as, for example, tissue or fluid isolated from an individual (including without limitation plasma, serum, cerebrospinal fluid, lymph, tears, saliva and tissue sections) or from in vitro cell culture constituents, as well as samples from the environment. The sample of nucleic acids can be drawn from any source and can be natural or synthetic. The sample of nucleic acids may contain of deoxyribonucleic acids (DNA), ribonucleic acids (RNA), or copolymers of deoxyribonucleic acids and ribonucleic acids or combinations thereof. Alternatively, the sample may have been subject to purification (e.g. extraction) or other treatment. The term "sample" can also refer to "a biological sample."

As used herein, the term "a biological sample" refers to a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). "A biological sample" further refers to a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. Most often, the sample has been removed from an animal, but the term "biological sample" can also refer to cells or tissue analyzed in vivo, i.e., without removal from animal. Typically, a "biological sample" will contain cells from the animal, but the term can also refer to non-cellular biological material, such as non-cellular fractions of blood, saliva, or urine, that can be used to measure the cancer-associated polynucleotide or polypeptides levels. "A biological sample" further refers to a medium, such as a nutrient broth or gel in which an organism has been propagated, which contains cellular components, such as proteins or nucleic acid molecules.

As used herein, the term "an increase of the signal" means that the signal generated from hybridization between two nucleic acids is greater than that generated from either one of said two nucleic acids alone in unhybridized form. Preferably, the hybridization is between a nucleic acid probe and a target nucleic acid. Also preferably, the hybridization is between a first nucleic acid and a second nucleic acid. Preferably, the increase is at least about 10%, preferably at least about 15%, about 25%, about 30%, about 40%, about 50%, about 65%, about 75%, about 85%, about 90%, about 95%, about more than 100%, about twofold, about ten fold, about fifty fold, or greater.

As used herein, the term "decrease of the signal" means that the signal generated from hybridization between two nucleic acids that are complementary but for a mismatch, is lower than that generated from hybridization between two completely complementary nucleic acids. Preferably, the decrease is at least about 10%, preferably at least about 15%, about 25%, about 30%, about 40%, about 50%, about 65%, about 75%, about 85%, about 90%, about 95%, about more than 100%, about twofold, about ten fold, about fifty fold, or greater.

As used herein, the term "a transition metal" refers to any of the elements found between the Group IIA Elements and the Group IIB Elements in the periodic table. Transition metals to be used in a transition metal complex of the present invention include those of the fourth, fifth, and sixth periods of the periodic table of elements. Preferably, the transition metals used in the present invention include iron, ruthenium, cobalt, molybdenum, osmium and rhenium.

As used herein, the term "transition metal complex" refers to a structure composed of a central transition metal atom or ion, generally a cation, surrounded by a number of negatively charged or neutral ligands possessing lone pairs electrons that can be given to the central metal. The transition metal is defined herein above. The ligands bind to the central transition metal using dative bonds. There are a number of different types of ligands that can be applied to the present invention. Non-limiting examples include but not limited to, monodentate ligands, bidendate ligands, tridendate ligands, tetradentate ligands and hexadentate ligands, etc. Preferably, the ligands can be pyridine-based, phenanthroline-based, heterocyclic, aquo, aromatic, chloride ($Cl^-$), or ammonia ($NH_3$), or cyanide ($CN^-$).

Described herein is an electrocatalytic detection assay that reports hybridization between nucleic acids, or between nucleic acids and proteins. In one aspect, the assay can be used to detect hybridization between a nucleic acid probe and a DNA or RNA target. The present assay is sufficiently sensitive to resolve single-base changes in the target sequence. The method exploits a reaction between a redox pair comprising a nucleic acid-binding compound and a redox-active probe. The nucleic acid-binding compound can be a transition metal complex. Preferably, the transition metal is one selected from the group consisting of cobalt, iron, molybdenum, osmium, ruthenium and rhenium. Also preferably, the transition metal complex is an ammonium complex of the transition metal. More preferably, the transition metal complex is $Ru(NH_3)_6^{3+}$. The redox active probe can also be a transition metal complex. Preferably, the transition metal is one selected from the group consisting of cobalt, molybdenum, osmium, iron and rhenium. Also preferably, the transition metal complex is a cynate complex of the transition metal. More preferably, the transition metal complex is $Fe(CN)_6^{-3}$.

The nucleic acid-binding compound binds to the nucleic acid primarily through electrostatic interactions with the phosphate backbone, and therefore its electrochemical reduction yields a signal that reports on the increase of negatively charged groups at the electrode surface upon hybridization of a target nucleic acid. The signal is amplified by the transition metal oxidant of the redox active probe which permits the transition metal to be regenerated for multiple cycles. The immobilization of the nucleic acid probe on highly conductive surfaces, e.g., gold, amplifies the kinetic effects of base mismatches on nucleic acid hybridization, permitting single-base changes to be resolved.

One advantage of the assay is the use of the nucleic acid-binding compound to report the hybridization event and the coupling of this signal to an electrocatalytic process. The design also provides superior sensitivity, e.g., detection of a single base mismatch.

The invention described herein is useful for the detection of infectious bacterial and viral agents. The invention is also useful in detecting genes and proteins, e.g., changes in genes and proteins, e.g., changes in oncogenes. It therefore is useful in a clinical diagnostic setting, and for detection of pathogenic agents in non-clinical settings, e.g., detection of bioterror agents.

In another aspect, the method described herein can be used to determine the presence of a target nucleic acid according to the following protocol. A biological sample suspected of containing the target nucleic acid may optionally be treated to release any nucleic acid contained within the sample. For instance, the sample can be serum, blood, other bodily fluids, tissue, etc. The sample can also be from a human, an animal, a plant, etc. The sample can also be nucleic acid washed from a swab or some other type of material used to wipe surfaces to detect contaminants. The sample can also be nucleic acid extracted or washed off of a filter through which air is passed, e.g. a filter from an air filtration system, in the case of detecting airborne bioterror agents. Such an article can be treated to extract the nucleic acid by methods that are known in the art, e.g., forensics and contamination detection. The nucleic acid extracted from the article can be tested directly by the methods described herein, or can be amplified to enhance detection.

In one embodiment, the invention features a method of detecting nucleic acid hybridization between a nucleic acid probe and a target nucleic acid in a sample, where the method includes the steps of: (a) providing a nucleic acid probe immobilized on a solid substrate; (b) contacting, under hybridizing conditions, the solid support and the immobilized probe to a solution containing the sample and a redox pair, wherein the redox pair comprises a first transition metal complex and a second transition metal complex; and (c) measuring the electrocatalytic signal generated by hybridization of the nucleic acid probe and the target nucleic acid; where an increase of the signal detected in step (c) relative to that of a control sample containing no nucleic acid, indicates that the nucleic acid hybridization has occurred. The method can also include an additional step of testing a control, by contacting, under hybridizing conditions, the solid support and the immobilized nucleic acid probe to a solution containing no sample, and a redox pair comprising a first transition metal complex and a second transition metal complex.

Preferably, the transition metal of the first transition metal complex is one selected from the group consisting of cobalt, iron, molybdenum, osmium, ruthenium and rhenium. More preferably, the transition metal of the first transition metal complex is ruthenium. Also preferably, the first transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

Preferably, the transition metal of the second transition metal complex is one selected from the group consisting of cobalt, molybdenum, osmium and rhenium. More preferably, the transition metal of the second transition metal complex is iron. Also preferably, the second transition metal complex is a transition metal cynate complex. More preferably, the second transition metal cynate complex comprises a transition metal selected from the group consisting of cobalt, molybdenum, osmium and rhenium. Most preferably, the second transition metal cynate complex is $Fe(CN)_6^{-3}$.

In another embodiment, the invention also features a method of detecting nucleic acid hybridization between a first nucleic acid and a second nucleic acid, wherein the method includes the steps of: (a) providing the first nucleic acid immobilized on a solid support; (b) contacting, under hybridizing conditions, the solid support and the immobilized first nucleic acid to a solution suspected of containing the second nucleic acid and a redox pair comprising a first transition metal complex and a second transition metal complex; and (c) measuring the electrocatalytic signal generated by hybridization of the first and second nucleic acids; wherein an increase of the signal detected in step (c) relative to that of an unhybridized first nucleic acid, indicates that nucleic acid hybridization has occurred. The method can also include an additional step of testing a control, by contacting, under hybridizing conditions, the solid support and the immobilized first nucleic acid to a solution containing no sample, and a redox pair comprising a first transition metal complex and a second transition metal complex.

Preferably, the transition metal of the first transition metal complex is one selected from the group consisting of cobalt, iron, molybdenum, osmium, ruthenium and rhenium. More preferably, the transition metal of the first transition metal complex is ruthenium. Also preferably, the first transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

Preferably, the transition metal of the second transition metal complex is one selected from the group consisting of cobalt, molybdenum, osmium and rhenium. More preferably, the transition metal of the second transition metal complex is iron. Also preferably, the second transition metal complex is a transition metal cynate complex. More preferably, the second transition metal cynate complex comprises a transition metal selected from the group consisting of cobalt, molybdenum, osmium and rhenium. Most preferably, the second transition metal cynate complex is $Fe(CN)_6^{-3}$.

In another aspect, the invention features a method of detecting a mismatch between a first nucleic acid and a second nucleic acid, comprising: (a) providing a nucleic acid probe immobilized on a solid support; (b) contacting, under hybridizing conditions, the solid support and the immobilized probe to a solution containing the sample containing a target nucleic acid and a redox pair, wherein the redox pair comprises a first transition metal complex and a second transition metal complex; and (c) measuring the electrocatalytic signal generated by hybridization of the nucleic acid probe and the target nucleic acid; wherein a decrease of the signal detected in step (c) relative to that of a perfect complementarity between the nucleic acid probe and the target nucleic acid, indicates that there is a mismatch between the first nucleic acid and the second nucleic acid. The method can also include an additional step of testing a control, by contacting, under hybridizing conditions, the solid support and the immobilized nucleic acid probe to a solution containing no sample, and a redox pair comprising a first transition metal complex and a second transition metal complex.

Preferably, the transition metal of the first transition metal complex is one selected from the group consisting of cobalt, iron, molybdenum, osmium, ruthenium and rhenium. More preferably, the transition metal of the first transition metal complex is ruthenium. Also preferably, the first transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

Preferably, the transition metal of the second transition metal complex is one selected from the group consisting of cobalt, molybdenum, osmium and rhenium. More preferably, the transition metal of the second transition metal complex is iron. Also preferably, the second transition metal complex is a transition metal cynate complex. More preferably, the second transition metal cynate complex comprises a transition metal selected from the group consisting of cobalt, molybdenum, osmium and rhenium. Most preferably, the second transition metal cynate complex is $Fe(CN)_6^{-3}$.

The invention additionally features a method of detecting a mismatch between a first nucleic acid and a second nucleic acid, wherein the method includes the following steps: (a) providing the first nucleic acid immobilized on a solid support; (b) contacting, under hybridizing conditions, the solid support and the immobilized first nucleic acid to a solution containing the sample containing the second nucleic acid and a redox pair, wherein the redox pair comprises a first transition metal complex and a second transition metal complex; and (c) measuring the electrocatalytic signal generated by hybridization of the first nucleic acid and the second nucleic acid; wherein a decrease of the signal detected in step (c) relative to that of a perfect complementarity between the first nucleic acid and the second nucleic acid, indicates that there is a mismatch between the first nucleic acid and the second nucleic acid. The method can also include an additional step of testing a control, by contacting, under hybridizing conditions, the solid support and the immobilized nucleic acid probe to a solution containing no sample, and a redox pair comprising a first transition metal complex and a second transition metal complex.

Preferably, the transition metal of the first transition metal complex is one selected from the group consisting of cobalt, iron, molybdenum, osmium, ruthenium and rhenium. More preferably, the transition metal of the first transition metal complex is ruthenium. Also preferably, the first transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

Preferably, the transition metal of the second transition metal complex is one selected from the group consisting of cobalt, molybdenum, osmium and rhenium. More preferably, the transition metal of the second transition metal complex is iron. Also preferably, the second transition metal complex is a transition metal cynate complex. More preferably, the second transition metal cynate complex comprises a transition metal selected from the group consisting of cobalt, molybdenum, osmium and rhenium. Most preferably, the second transition metal cynate complex is $Fe(CN)_6^{-3}$.

In another embodiment, the invention also features a method of detecting nucleic acid hybridization between a nucleic acid probe and a target nucleic acid, where the method includes the following steps: (a) providing a nucleic acid probe immobilized on a solid support; (b) contacting the immobilized probe to a solution containing: (i) a transition metal complex; (c) measuring the electrocatalytic signal generated; (d) contacting the immobilized probe to a solution containing: (i) a sample thought to include the target nucleic acid, and (ii) a transition metal complex; (e) measuring the electrocatalytic signal generated; wherein an increase in the signal detected in step (e) over the signal generated in step (c) indicates that hybridization between the nucleic acid probe and the target nucleic acid has occurred. Preferably, the transition metal of the transition metal complex is one selected from the group consisting of cobalt, iron, molybdenum, osmium, ruthenium and rhenium. More preferably, the transition metal of the transition metal complex is ruthenium. Also preferably, the transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

The solutions can also include a second transition metal complex to enhance the electrocatalytic signal generated. Preferably, the transition metal of the second transition metal complex is one selected from the group consisting of cobalt, molybdenum, osmium and rhenium. More preferably, the transition metal of the second transition metal complex is iron. Also preferably, the second transition metal complex is a transition metal cynate complex. More preferably, the second transition metal cynate complex comprises a transition metal selected from the group consisting of cobalt, molybdenum, osmium and rhenium. Most preferably, the second transition metal cynate complex is $Fe(CN)_6^{-3}$.

The method can also include rinsing steps, e.g., rinsing the electrode between contact with the different solutions.

Another aspect of the invention additionally features a method of detecting the presence of a target nucleic acid in a sample, wherein the method includes the following steps: (a) providing a nucleic acid probe immobilized on a solid support; (b) contacting the immobilized probe to a solution containing: (i) a transition metal complex; (c) measuring the electrocatalytic signal generated; (d) contacting the immobilized probe to a solution containing: (i) a sample thought to include the target nucleic acid, and (ii) a transition metal complex; (e) measuring the electrocatalytic signal generated; wherein an increase in the signal detected in step (e) over the signal generated in step (c) indicates the target nucleic acid is present in the sample. Preferably, the transition metal of the transition metal complex is one selected from the group consisting of cobalt, iron, molybdenum, osmium, ruthenium and rhenium. More preferably, the transition metal of the transition metal complex is ruthenium. Also preferably, the transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

The solutions can also include a second transition metal complex to enhance the electrocatalytic signal generated. Preferably, the transition metal of the second transition metal complex is one selected from the group consisting of cobalt, molybdenum, osmium and rhenium. More preferably, the transition metal of the second transition metal complex is iron. Also preferably, the second transition metal complex is a transition metal cynate complex. More preferably, the second transition metal cynate complex comprises a transition metal selected from the group consisting of cobalt, molybdenum, osmium and rhenium. Most preferably, the second transition metal cynate complex is $Fe(CN)_6^{-3}$.

The method can also include rinsing steps, e.g., rinsing the electrode between contact with the different solutions.

The invention further features a method of detecting a mismatch between two nucleic acids, where the method includes the following steps: (a) providing a nucleic acid probe immobilized on a solid support; (b) contacting the immobilized probe to a solution containing: (i) a transition metal complex; (c) measuring the electrocatalytic signal generated; (d) contacting the immobilized probe to a solution containing: (i) a sample thought to include the target nucleic acid, and (ii) a transition metal complex; (e) measuring the electrocatalytic signal generated; wherein a decrease in the signal detected in step (e) over the signal generated in step (c) indicates that there is a mismatch between the nucleic acid probe and the target nucleic acid. Preferably, the transition metal of the transition metal complex is one selected from the group consisting of cobalt, iron, molybdenum, osmium, ruthenium and rhenium. More preferably, the transition metal of the transition metal complex is ruthenium. Also preferably, the transition metal complex is a transition metal ammonium complex. More preferably, the first transition metal ammonium complex comprises a transition metal selected from the group consisting of cobalt, iron, molybdenum, osmium, ruthenium and rhenium. Most preferably, the transition metal ammonium complex is $Ru(NH_3)_6^{3+}$.

The solutions can also include a second transition metal complex to enhance the electrocatalytic signal generated. Preferably, the transition metal of the second transition metal complex is one selected from the group consisting of cobalt, molybdenum, osmium and rhenium. More preferably, the transition metal of the second transition metal complex is iron. Also preferably, the second transition metal complex is a transition metal cynate complex. More preferably, the second transition metal cynate complex comprises a transition metal selected from the group consisting of cobalt, molybdenum, osmium and rhenium. Most preferably, the second transition metal cynate complex is $Fe(CN)_6^{-3}$.

The method can also include rinsing steps, e.g., rinsing the electrode between contact with the different solutions.

In any of the methods described herein, the solid support can be a gold electrode.

The target nucleic acid that is detected by the method of the present invention can be, for example, single-stranded or double-stranded DNA, single-stranded or double-stranded RNA, or a hybrid of DNA and RNA. The target also can be a polynucleotide, e.g., in a purified or non-purified form. The sample of nucleic acids can be drawn from any source and can be natural or synthetic. The sample of nucleic acid may contain deoxyribonucleic acids (DNA), ribonucleic acids (RNA), or copolymers of deoxyribonucleic acid and ribonucleic acid or combinations thereof. The target polynucleotide can be synthesized enzymatically or chemically in vitro, or be synthesized non-enzymatically. The sample containing the target polynucleotide can also comprise extragenomic DNA from an organism, RNA transcripts thereof, or cDNA prepared from RNA transcripts thereof. Also, the target polynucleotide can be synthesized by the polymerase or ligase chain reaction.

Preferably, the nucleic acid probe is a sequence that is known to be unique to the target nucleic acid (e.g., pathogen) being detected. Such unique sequences are known for a number of pathogens, and methods for obtaining such unique sequences are also known (see, e.g., U.S. Pat. No. 4,900,659, "Nucleotide sequence composition and method for detection of *Neisseria gonorrhoea* and method for screening for a nucleotide sequence that is specific for a genetically distinct group"). The probe sequence is capable of binding to the target nucleic acid of complementary sequence through one or more types of chemical bonds including base pairing.

Among the target nucleic acid which can be detected using the molecular probe of the invention is genetic material in the form of DNA or RNA obtained from any naturally occurring prokaryotes such as for example, pathogenic or non-pathogenic bacteria including but not limited to species of *Escherichia, Salmonella, Clostridium, Chlamydia*, etc., eukaryotes such as for example, protozoans and parasites, fungi, yeast, higher plants, insects, lower and higher animals, including mammals and humans and cells in tissue culture, or viruses such as for example, Herpes viruses, HIV, influenza virus, Epstein-Barr virus, hepatitis B virus, etc.

Target nucleic acids from these sources may, for example, be found in samples of a bodily fluid from an animal, including a human, such as, but not limited to, blood, urine, lymphatic fluid, synovial fluid, bile, phlegm, saliva, menstrual fluid and semen. In addition, samples containing DNA or RNA may, for example, be found in fluids from a plant, such as, but not limited to, xylem fluid, phloem fluid and plant exudates. Samples containing DNA or RNA may, for example also be found in non-living sources such as, but not limited to, food, sewage, forensic samples, lakes, reservoirs, rivers and oceans. Target polynucleotides can also be those of defunct or extinct organisms, e.g., pressed plants in herbarium collections, or from pelts, taxidermy displays, fossils, or those of biological materials in museum collections.

The target nucleic acid molecule may optionally be amplified prior to detection by the method of the present invention. The target nucleic acid can be in either a double-stranded or single-stranded form. In the case where the target nucleic acid molecule is double-stranded, it is preferably first treated by a denaturation agent to render the two strands into a single-stranded, or partially single-stranded form, at the start of the amplification reaction, by methods known in the art such as heating, alkali treatment, or by enzymatic methods. General methods for accomplishing this treatment are provided by Sambrook, J. et al., *Molecular Cloning: A Laboratory Manual*, Cold Spring Harbor Laboratory Press, Cold Spring Harbor, N.Y., U.S.A. (1989).

Once the sample has been treated to expose any target nucleic acid, the solution can be tested as described herein to detect hybridization between the attached nucleic acid and the target nucleic acid, if such is present. Alternatively, some samples can be tested directly, e.g., the target may exist in a serum sample and can be directly accessible, and may not require treatment to release the nucleic acid.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., *Molecular Cloning: A Laboratory Manual*, Cold Spring Harbor Laboratory Press). The conditions of temperature and ionic strength determine the "stringency" of the hybridization. For preliminary screening for homologous nucleic acids, low stringency hybridization conditions, corresponding to a $T_m$ of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementary, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8). Preferably a minimum length for a hybridizable nucleic acid is at least about 10 nucleotides; preferably at least about 15 nucleotides; and more preferably the length is at least about 20 nucleotides; and most preferably 30 nucleotides.

"High stringency hybridization conditions" can employ hybridization at either (1) 1×SSC (10×SSC=3 M NaCl, 0.3 M $Na_3$-citrate.$2H_2O$ (88 g/liter), pH to 7.0 with 1 M HCl), 1% SDS (sodium dodecyl sulfate), 0.1-2 mg/ml denatured salmon sperm DNA at 65° C., (2) 1×SSC, 50% formamide, 1% SDS, 0.1-2 mg/ml denatured salmon sperm DNA at 42° C., (3) 1% bovine serum albumen (fraction V), 1 mM $Na_2$.EDTA, 0.5 M $NaHPO_4$ (pH 7.2) (1 M $NaHPO_4$=134 g $Na_2HPO_4.7H_2O$, 4 ml 85% $H_3PO_4$ per liter), 7% SDS, 0.1-2 mg/ml denatured salmon sperm DNA at 65° C., (4) 50% formamide, 5×SSC, 0.02 M Tris-HCl (pH 7.6), 1×Denhardt's solution (100×=10 g Ficoll 400, 10 g polyvinylpyrrolidone, 10 g bovine serum albumin (fraction V), water to 500 ml), 10% dextran sulfate, 1% SDS, 0.1-2 mg/ml denatured salmon sperm DNA at 42° C., (5) 5×SSC, 5×Denhardt's solution, 1% SDS, 100 g/ml denatured salmon sperm DNA at 65° C., or (6) 5×SSC, 5×Denhardt's solution, 50% formamide, 1% SDS, 100 µg/ml denatured salmon sperm DNA at 42° C., with high stringency washes of either (1) 0.3-0.1×SSC, 0.1% SDS at 65° C., or (2) 1 mM $Na_2$EDTA, 40 mM $NaHPO_4$ (pH 7.2), 1% SDS at 65° C. The above conditions are intended to be used for DNA-DNA hybrids of 50 base pairs or longer. Where the hybrid is believed to be less than 18 base pairs in length, the hybridization and wash temperatures should be 5-10° C. below that of the calculated $T_m$ of the hybrid, where $T_m$ in ° C.=(2× the number of A and T bases)+(4× the number of G and C bases). For hybrids believed to be about 18 to about 49 base pairs in length, the $T_m$ in ° C.=(81.5° C.+16.6($\log_{10}$M)+0.41(% G+C)−0.61(% formamide)−500/L), where "M" is the molarity of monovalent cations (e.g., Na$^+$), and "L" is the length of the hybrid in base pairs.

"Moderate stringency hybridization conditions" can employ hybridization at either (1) 4×SSC, (10'SSC=3 M NaCl, 0.3 M Na$_3$-citrate.2H$_2$O (88 g/liter), pH to 7.0 with 1 M HCl), 1% SDS (sodium dodecyl sulfate), 0.1-2 mg/ml denatured salmon sperm DNA at 65° C., (2) 4×SSC, 50% formamide, 1% SDS, 0.1-2 mg/ml denatured salmon sperm DNA at 42° C., (3) 1% bovine serum albumen (fraction V), 1 mM Na$_2$.EDTA, 0.5 M NaHPO$_4$ (pH 7.2) (1 M NaHPO$_4$=134 g Na$_2$HPO$_4$.7H$_2$O, 4 ml 85% H$_3$PO$_4$ per liter), 7% SDS, 0.1-2 mg/ml denatured salmon sperm DNA at 65° C., (4) 50% formamide, 5×SSC, 0.02 M Tris-HCl (pH 7.6), 1×Denhardt's solution (100×=10 g Ficoll 400, 10 g polyvinylpyrrolidone, 10 g bovine serum albumin (fraction V), water to 500 ml), 10% dextran sulfate, 1% SDS, 0.1-2 mg/ml denatured salmon sperm DNA at 42° C., (5) 5×SSC, 5×Denhardt's solution, 1% SDS, 100 µg/ml denatured salmon sperm DNA at 65° C., or (6) 5×SSC, 5×Denhardt's solution, 50% formamide, 1% SDS, 100 µg/ml denatured salmon sperm DNA at 42° C., with moderate stringency washes of 1×SSC, 0.1% SDS at 65° C. The above conditions are intended to be used for DNA-DNA hybrids of 50 base pairs or longer. Where the hybrid is believed to be less than 18 base pairs in length, the hybridization and wash temperatures should be 5-10° C. below that of the calculated $T_m$ of the hybrid, where $T_m$ in ° C.=(2× the number of A and T bases)+(4× the number of G and C bases). For hybrids believed to be about 18 to about 49 base pairs in length, the $T_m$ in ° C.=(81.5° C.+16.6(log$_{10}$M)+0.41(% G+C)−0.61(% formamide)−500/L), where "M" is the molarity of monovalent cations (e.g., Na$^+$), and "L" is the length of the hybrid in base pairs.

"Low stringency hybridization conditions" can employ hybridization at either (1) 4×SSC, (10×SSC=3 M NaCl, 0.3 M Na$_3$-citrate.2H$_2$O (88 g/liter), pH to 7.0 with 1 M HCl), 1% SDS (sodium dodecyl sulfate), 0.1-2 mg/ml denatured salmon sperm DNA at 50° C., (2) 6×SSC, 50% formamide, 1% SDS, 0.1-2 mg/ml denatured salmon sperm DNA at 40° C., (3) 1% bovine serum albumen (fraction V), 1 mM Na$_2$.EDTA, 0.5 M NaHPO$_4$ (pH 7.2) (1 M NaHPO$_4$=134 g Na$_2$HPO$_4$.7H$_2$O, 4 ml 85% H$_3$PO$_4$ per liter), 7% SDS, 0.1-2 mg/ml denatured salmon sperm DNA at 50° C., (4) 50% formamide, 5×SSC, 0.02 M Tris-HCl (pH 7.6), 1×Denhardt's solution (100×=10 g Ficoll 400, 10 g polyvinylpyrrolidone, 10 g bovine serum albumin (fraction V), water to 500 ml), 10% dextran sulfate, 1% SDS, 0.1-2 mg/ml denatured salmon sperm DNA at 40° C., (5) 5×SSC, 5×Denhardt's solution, 1% SDS, 100 µg/ml denatured salmon sperm DNA at 50° C., or (6) 5×SSC, 5×Denhardt's solution, 50% formamide, 1% SDS, 100 µg/ml denatured salmon sperm DNA at 40° C., with low stringency washes of either 2×SSC, 0.1% SDS at 50° C., or (2) 0.5% bovine serum albumin (fraction V), 1 mM Na$_2$EDTA, 40 mM NaHPO$_4$ (pH 7.2), 5% SDS. The above conditions are intended to be used for DNA-DNA hybrids of 50 base pairs or longer. Where the hybrid is believed to be less than 18 base pairs in length, the hybridization and wash temperatures should be 5-10° C. below that of the calculated $T_m$ of the hybrid, where $T_m$ in ° C.=(2× the number of A and T bases)+(4× the number of G and C bases). For hybrids believed to be about 18 to about 49 base pairs in length, the $T_m$ in ° C.=(81.5° C.+16.6(log$_{10}$M)+0.41(% G+C)−0.61(% formamide)−500/L), where "M" is the molarity of monovalent cations (e.g., Na$^+$), and "L" is the length of the hybrid in base pairs.

The assays described herein can be used to detect pathogens, such as bacteria or viruses, or can be used to detect the expression of genes in a subject. For instance, genes from *Helicobacter pylori*, a pathogen implicated in gastric ulcers and cancer, were detected by the methods described herein. Two sequences belonging to the pathogenic microbe *Helicobacter pylori* are used to demonstrate the versatility and specificity of the assay: one that codes for an unique *H. pylori* protein and one that represents a small portion of the 23S rRNA from this organism. Both sequences can be detected into the nanomolar concentration range. In addition to reporting the presence of pathogen-related sequences, this assay can accurately resolve single-base changes in target sequences. An A2143C substitution within the *H. pylori* rRNA that confers antibiotic resistance significantly attenuates hybridization to an immobilized probe corresponding to the WT sequence. The single base mismatch introduced by this mutation slows the kinetics of hybridization and permits discrimination of the two sequences at short hybridization times. The assay described may therefore provide a means to detect and genotype infectious bacteria using electrochemical methods.

Figure 2B:
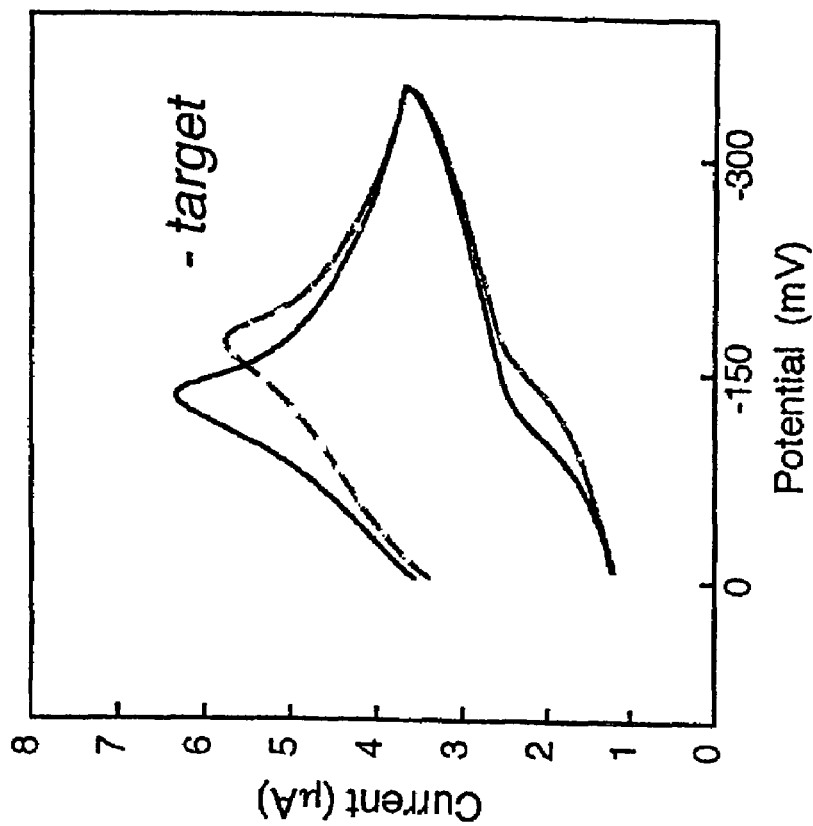
FIGS. 2A and 2B shows electrocatalytic hybridization detection of the Hpn sequence from *H. pylori*.
Figure 2A:
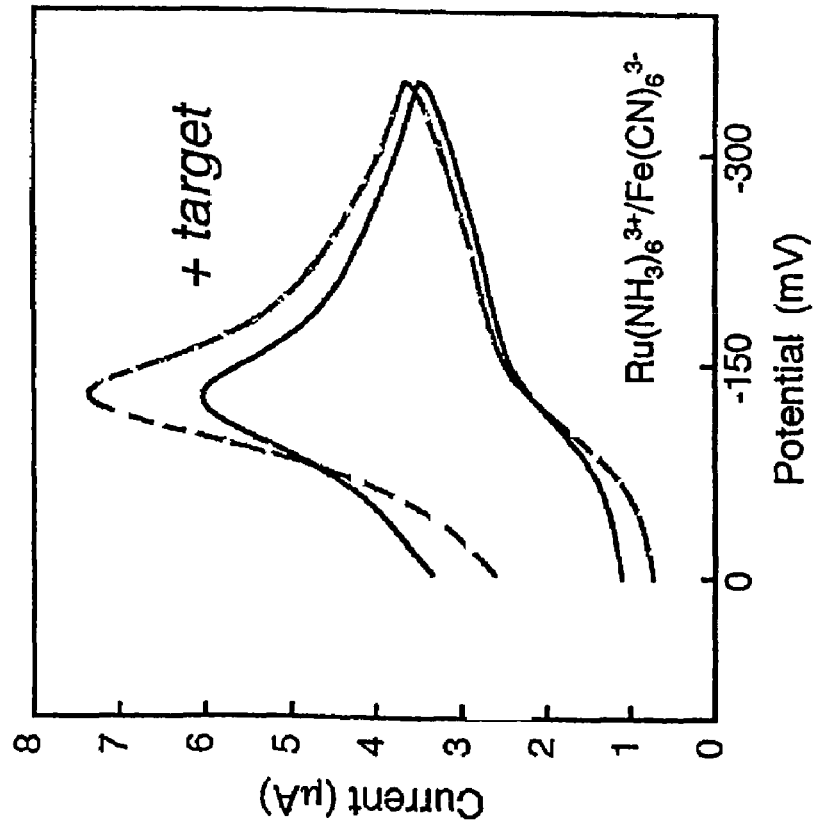

FIG. 1 shows a schematic of the electrocatalytic DNA hybridization detection system of the invention, which uses the increased loading of Ru(NH$_3$)$_6^{3+}$ resulting from the formation of a DNA duplex to report hybridization. The introduction of Fe(CN)$_6^{3-}$ makes the electrochemical reduction of this cation catalytic and amplifies the signal dramatically. FIG. 2 illustrates representative data obtained using this approach to detect a synthetic 30-mer modeling the Hpn gene from *Helicobactor pylori*, an infectious bacterium that is strongly linked with gastric ulcers and cancer. Gold electrodes were modified with single-stranded probe sequence, the electrodes treated with mercaptohexanol, and incubated in two heated buffer solutions (one which contained the target sequence (FIG. 2A), and the other which did not (FIG. 2B). Hybridization conditions were 40° C., 35 mM sodium phosphate, 100 mM NaCl, 25 Minutes, with or without 4 µM Hpn target sequence:

5'-TGT TGC AGC ACT AGC GAT AGT CAT CAT CAA-3' (SEQ ID NO: 1)

Figure 3:
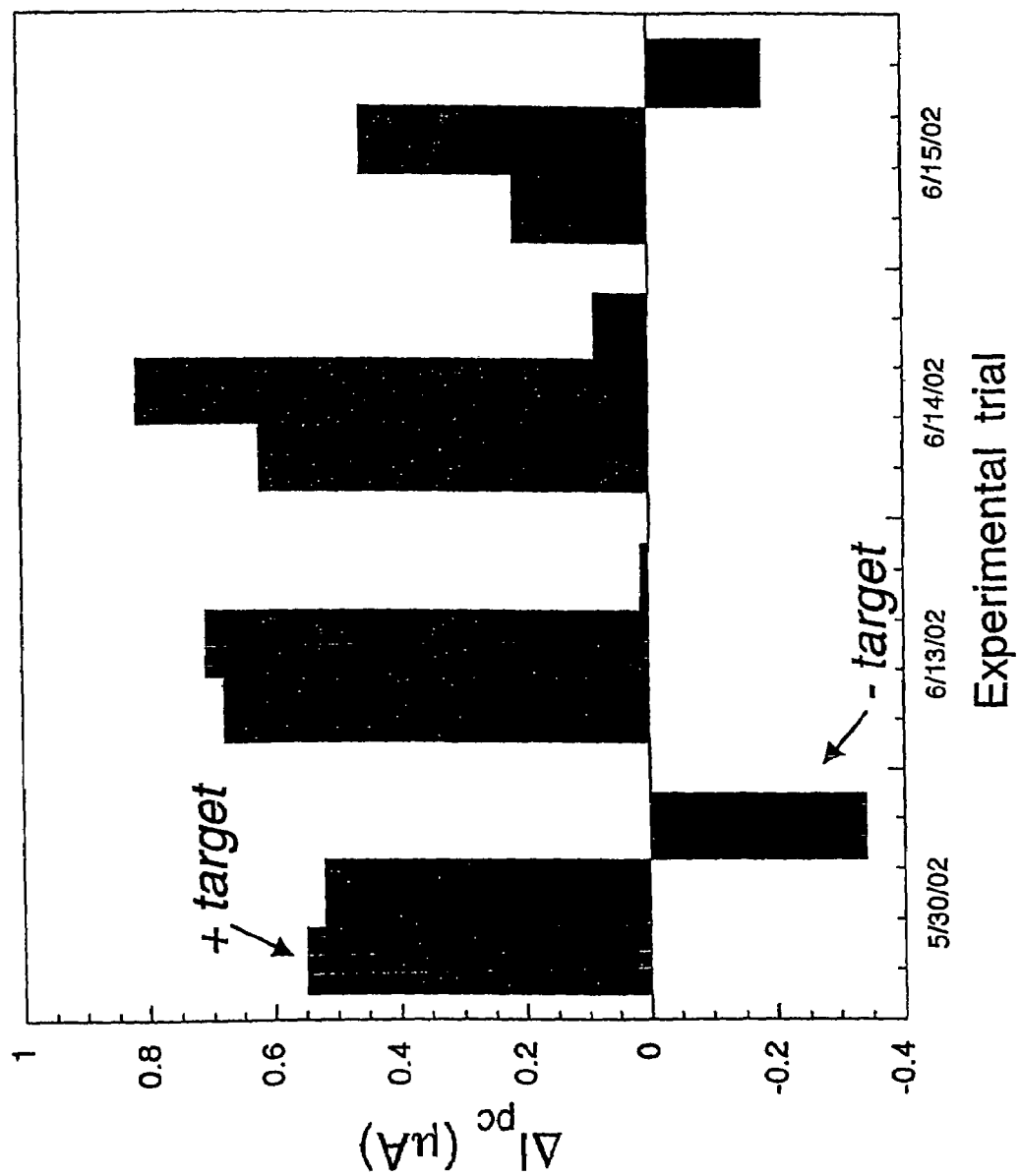
FIG. 3 is a histogram showing the reproducibility of the electrocatalytic hybridization detection. The tests described below and shown in FIG. 2 were performed on four different days.

The electrode exposed to the target sequence exhibited a pronounced increase in the electrochemical response, while that incubated in a buffer solution displayed a decreased response (this is a reproducible event—it appears that the heat treatment dislodges some loosely bound probe DNA). FIG. 3 shows the excellent reproducibility of the assay.

The invention is further illustrated by the following examples, which are not intended to be limiting.

EXAMPLES

Example 1

Materials and Methods

Chemicals and materials. DNA synthesis reagents were obtained from Glen Research. 1,6-hexamethylenediamine, 99.8% anhydrous 1,4-dioxane, 6-mercapto-1-hexanol (97%) (MCH), and potassium ferrocyanide trihydrate were received from Aldrich Chemical Company. Potassium ferricyanide, 1,1'-carbonyldiimidizole, and hexaammineruthenium chloride were purchased from Acros Organics. N-succinimidyl 3-(2-pyridyldithio)propionate (SPDP) was purchased from Pierce. Dithiothreitol (DTT) and 2-mercaptoethanol were obtained from Fisher Scientific. Gold-coated silicon wafers were received from Platypus Technologies. Cloned Pfu DNA polymerase was obtained from Stratagene.

Preparation and purification of modified oligonucleotides. Oligonucleotides were synthesized using an ABI 394 DNA/RNA synthesizer according to standard automated solid-phase techniques. Oligonucleotides modified at the 5'-terminus with hexanediamine-based linker (C6) were prepared and purified as described previously.[25] All unmodified oligonucleotides were stringently purified using reversed phase HPLC. The following probe and target sequences were used in experiments employing synthetic oligonucleotides:

HP1a (30 nt complementary hpn probe):
SH-5'TTGATGATGACTATCGCTAGTGCTGCAACA3' (SEQ ID NO: 12)

HP1b (18 nt+12T complementary hpn probe)
SH-5'TTTTTTTTTTTTGATGACTATCGCTAGTGC3' (SEQ ID NO: 4)

HP1c (18 nt+12T noncomplementary hpn probe)
SH-5'TTTTTTTTTTTTGGGATAATTCTTCACCGG3' (SEQ ID NO: 5)

HP2a (rRNA probe): SH-5'GGGTCTTTCCGTCTTGCC3' (SEQ ID NO: 13)

HP2b (rRNA probe-2): SH-5'GGTC-CACGGGGTCTTTCC3' (SEQ ID NO: 14)

T1 (hpn target) 5'TGTTGCAGCACTAGCGATAGTCAT-CATCAA3' (SEQ ID NO: 1)

T2a (WT rRNA target): 5'GGCAAGACGGAAA-GACCC3' (SEQ ID NO: 2)

T2aMUT (A2143C rRNA target): 5'GGCAAGACGGA$\underline{C}$AGACCC3' (SEQ ID NO: 3)

T2b (WT rRNA target #2): 5'GGAAAGACCCCGTG-GACC3' (SEQ ID NO: 15)

T2bMUT (A2143C rRNA target #2): 5'GGA$\underline{C}$AGACCCCGTGGACC3'
(SEQ ID NO: 16)

(in both A2143C rRNA sequences, the site of the resistance mutation is underlined.)

T-NC (noncomplementary target): 5'AAC AGT TCC TGC ATG3' (SEQ ID NO: 17)

Probe strands featuring fluorescein attached to the base at the 3'-terminus were synthesized using a fluorescein-dT CPG (Glen Research) and modified with a thiol-terminated linker as described previously. Fluorescein attachment to target strands was achieved with a 5'-fluorescein phosphoramidite following standard automated solid phase techniques. Fluorescein-modified oligonucleotides were purified by reversed phase HPLC.

Modification of gold surfaces with probe DNA. Single-stranded thiolated probes were immobilized on bulk gold electrodes with A=0.02 cm² (Bioanalytical Systems). Prior to probe immobilization, gold electrodes were polished using 0.05 μm alumina, rinsed in water, sonicated for 5 mm, etched by scanning from 0-1.8 V at 200 mV/sec in 1M $H_2SO_4$, and rinsed with water. Inverted gold electrodes were typically exposed to ssDNA thiolated probes in solutions containing 5 μM SH-DNA, 500 nM MCH, 25 mM sodium phosphate (pH 7), 25 mM NaCl, and 50 mM $MgCl_2$ in a humidity chamber at room temperature for 1 hour. (Any deviations from these conditions are described in individual figure captions.) Manipulation of probe film densities was achieved with solutions containing variable amounts of $MgCl_2$ ranging from 10-100 mM. Following deposition, electrodes were rinsed in 25 mM sodium phosphate (pH 7), 25 mM NaCl buffer. The adsorption of DNA on the electrode surface was confirmed by monitoring the blocking of 2 mM ferrocyanide in 25 mM sodium phosphate (pH 7), 25 mM NaCl.

Hybridization of target sequences. Gold electrodes modified with thiolated ssDNA were exposed to target sequences and hybridization was detected through enhancement of the electrocatalytic signal. Prior to hybridization of target, initial electrocatalytic measurements of immobilized ssDNA probes were recorded and upon hybridization of target the change in signal could be calculated.

Electrochemical measurements. Electrochemical measurements were conducted with a Bioanalytical Systems CV-50 potentiostat. A one-compartment cell fitted with a Luggin capillary was used. All cyclic voltammetry measurements were conducted at room temperature with a Bioanalytical Systems CV-50W potentiostat. A three-electrode configuration was used consisting of a modified gold working electrode, a platinum wire auxiliary electrode, and an Ag/AgCl reference electrode. A one-compartment cell fitted with a Luggin capillary was used to separate the working compartment from the reference compartment.

Electrocatalytic currents were measured in solutions of 2 mM $Fe(CN)_6^{3-}$, 27 μM $Ru(NH_3)_6^{3+}$ in 25 mM sodium phosphate/250 mM NaCl (pH 7) at a scan rate of 100 mV/s. Cathodic charge (Q) was quantitated by integrating background-subtracted voltammograms. Signal changes corresponding to hybridization were calculated as follows $\Delta Q = (Q_{final} - Q_{initial})/Q_{initial}$. Error bars shown on individual figures correspond to variabilities among multiple independent trials of each experiment.

Electrochemical Detection of Target Hybridization

The electrocatalytic current obtained at gold electrodes modified with thiolated probe DNA was measured, and rinsed electrodes were then exposed to target sequences and hybridization was detected through enhancement of the electrocatalytic signal. Hybridization solutions typically contained 500 mM-20 μM target DNA in 25 mM sodium phosphate (pH 7), 25 mM NaCl, 100 mM $MgCl_2$. Electrodes were incubated at 37-50° C. in a thermostatted humidity chamber and were washed extensively with buffer before electrochemical analysis. The conditions used for individual experiments varied depending on the size and source of the target nucleic acid; details of different hybridization trials are provided in the figure captions.

Fluorescence-Based Quantitation of Surface Coverage and Hybridization Efficiencies Quanatitation of electrode surface coverage using fluorescein-labeled DNA was achieved based on the procedure described by Demers et al. Prior to the deposition of fluorophore-labeled DNA, bulk gold electrodes were prepared as described above with electrochemical etching. Larger (0.28 cm²) flat gold surfaces were cleaned in Piranha solution (3:1 $H_2SO_4/H_2O_2$) for 20 minutes followed by stringent washing in water. Using a guide producing an area of 0.28 cm², 3'-fluorescein-5'-thiol modified oligonucleotide was incubated on the gold surface for 1 hour at room temperature in a humidity chamber. Probe immobilization was performed using a solution containing 5 μM 3'-fluorescein-5'-thiol probe, 500 nM MCH, 25 mM sodium phosphate (pH 7), 25 mM NaCl and varied amounts of $MgCl_2$ (10 mM to 100 mM). Substrates treated with noncomplementary probes were used as controls. After deposition, gold surfaces were washed extensively with 25 mM sodium phosphate (pH 7), 25 mM NaCl. Fluorophore-modified probes were then displaced with 12 mM mercaptoethanol for approximately 3-4 hours at room temperature in a humidity chamber; a second round of displacement was conducted overnight. Fluorescence intensities for calibration standards and samples removed from the gold surface were measured in 50 mM NaOH (pH 12) on a Wallac VictorF fluorescence plate reader. Amounts of 3'-fluorescein-5'-thiol modified oligonucleotide displaced from the surface were determined by interpolation from a standard linear calibration curve prepared with known concentrations of the modified probe.

For the measurement of hybridization efficiencies using fluorescence, labeled target sequences were introduced from solutions containing 5 μM target (F1–T2), 25 mM sodium phosphate (pH 7), 25 mM NaCl, and 100 mM $MgCl_2$ for 1 hour in a 40° C. incubator. The surfaces were then stringently washed with 25 mM sodium phosphate (pH 7), 25 mM NaCl to remove non-hybridized target. Displacement of duplexes and fluorescence measurements were performed as described above. A standard linear calibration curve was plotted using known concentrations of duplex DNA (HP2a/F1–T2).

Thermal Denaturation of Probe/Target Duplexes

Thermal denaturation measurements were performed with solutions containing 1 μM of complementary strands in 25 mM sodium phosphate (pH 7), 25 mM NaCl. Measurements were obtained by monitoring absorbance at 260 nM on an AVIV spectrophotometer.

Example 2

Fabrication of DNA-Modified Surfaces

The appendage of a thiol-terminated linker to synthetic oligonucleotides permits the self-assembly of DNA films on gold electrodes. Gold surfaces modified with single-stranded oligonucleotides have been prepared by several groups interested in monitoring electrochemical processes in the presence of DNA. The films used in the experiments described here feature oligonucleotides containing an aliphatic linker that is attached post-synthetically using a combination of solid- and solution-phase synthesis. A co-adsorbent, mercaptohexanol, is introduced during deposition to decrease the density of adsorbed DNA and to minimize non-specific DNA binding at the gold surface.

The conditions employed here for deposition produce high-density films from thiol-modified oligonucleotides within minutes and have coverages that depend on the amount of divalent cation used in the deposition solution. Using fluorescein-modified oligonucleotides, it was determined that densities of 12(±2), 23(±3), and 27(±4) pmol/cm² of single-stranded oligonucleotides were obtained with 10, 50, or 100 mM $MgCl_2$ present in the deposition buffer, respectively. Probe-density measurements were made both on bulk gold electrodes and vapor-deposited gold substrates to confirm that comparable densities existed (working with the larger substrates was desirable for more accurate quantitation of the less dense coverages). Coverages comparable to those measured here with low [$Mg^{2+}$] were observed in previous studies where deposition was performed in the presence of 10 mM sodium phosphate and 100 mM NaCl.

For the electrochemical experiments described below, DNA films were used that were formed with 50 mM $MgCl_2$ present during deposition. While sparser surface coverages promote more efficient DNA hybridization (vide infra), greater reproducibility was achieved with higher DNA densities that produced larger voltammetric signals.

Example 3

Detection of Target DNA Sequences Based on the Electrocatalytic Reduction of $Ru(NH_3)_6^{3+}$ at DNA-Modified Surfaces $Ru(NH_3)_6^{3+}$, lacking any ligands that can bind to DNA intercalatively, associates electrostatically with the negatively charged backbone. It is therefore a sequence-neutral binder and an ideal probe for quantitating DNA adsorbed on an electrode surface.[26] Monitoring hybridization with $Ru(NH_3)_6^{3+}$ would potentially provide a means to detect DNA electrochemically. However, the films with sparser surface coverages that permit efficient hybridization only yield small signals for this redox-active species.

Figure 4:
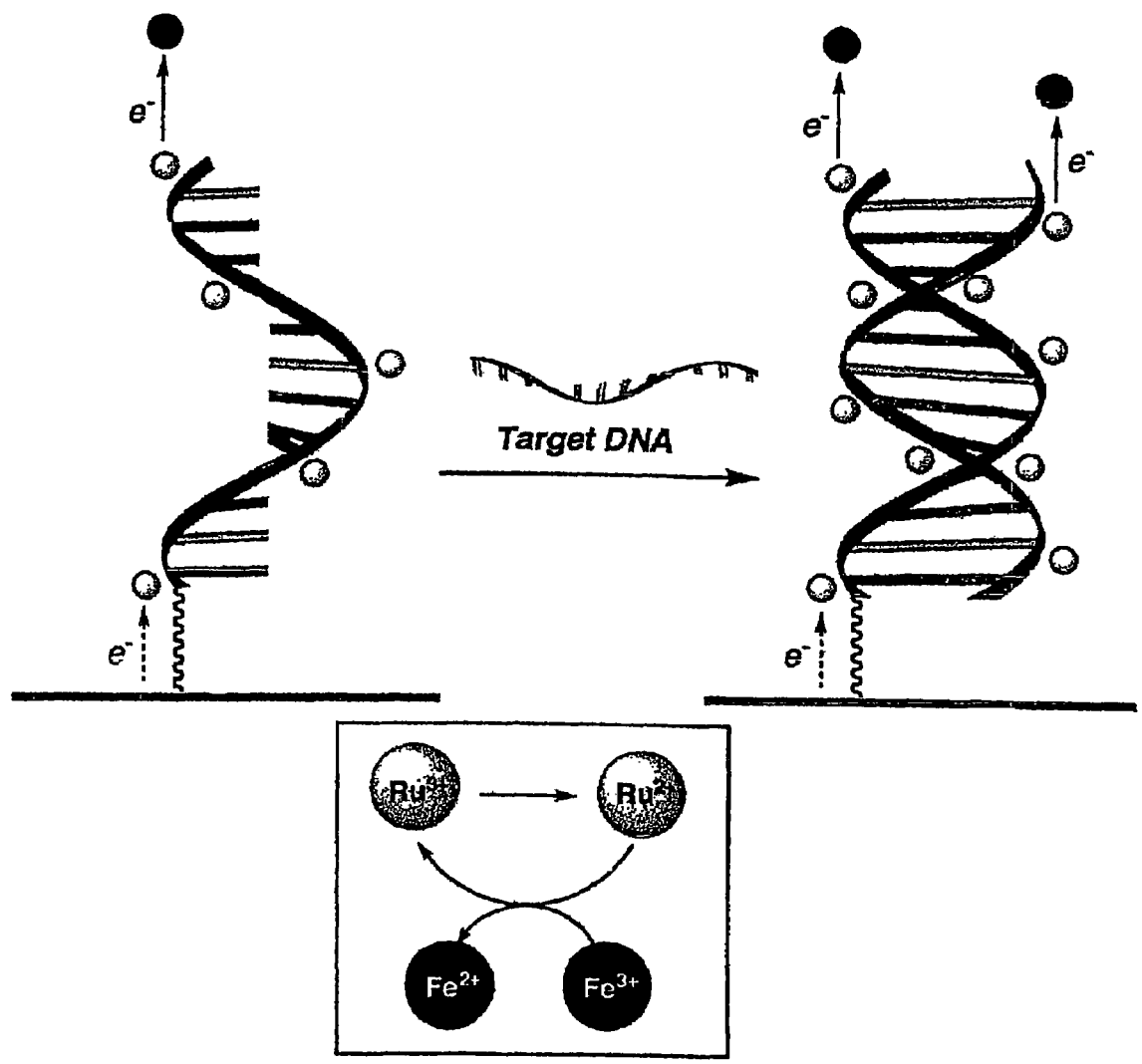
FIG. 4 is an illustration of electrocatalytic detection of DNA hybridization.
Figure 6:
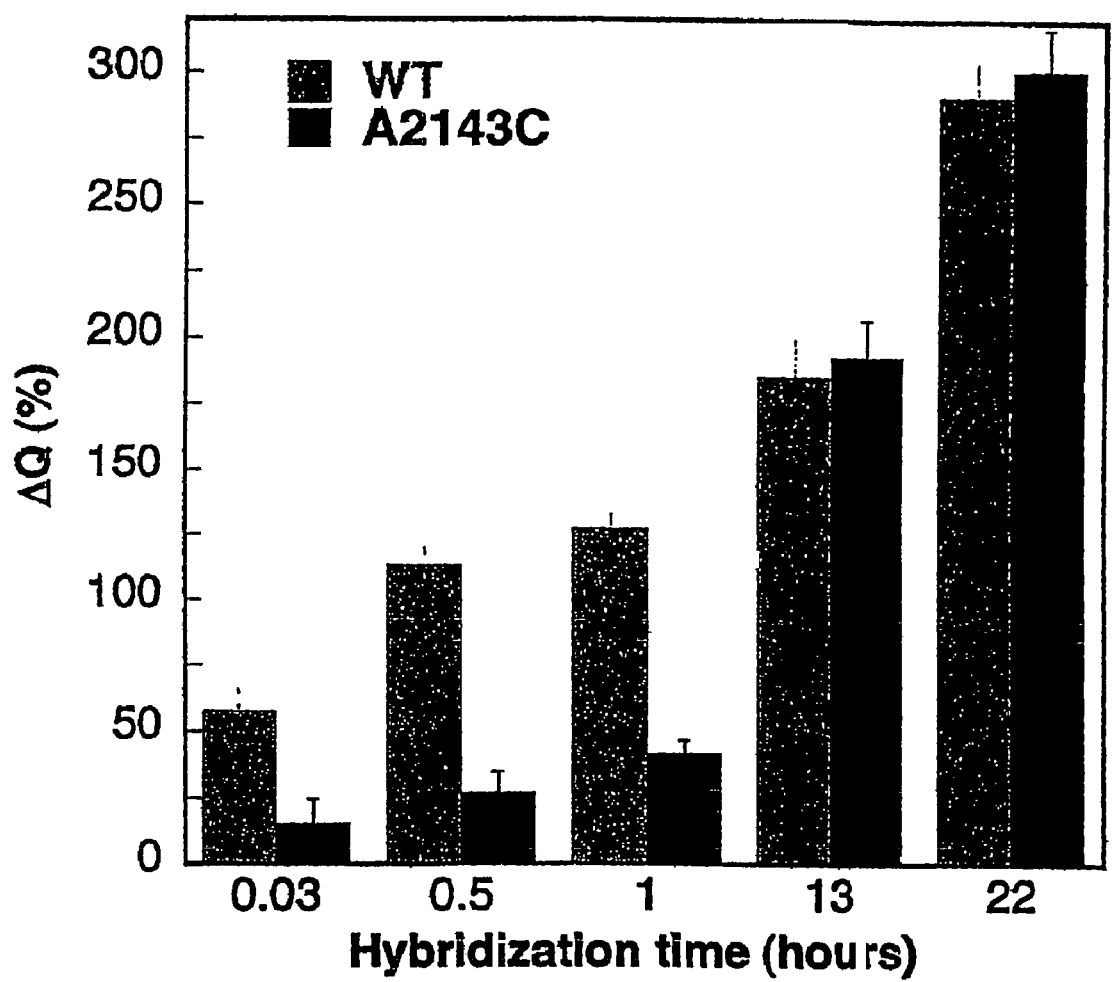
FIG. 6 is a bar graph showing the time dependence of hybridization for WT and A2143C sequences corresponding to a fragment of the *H. pylori* 23S rRNA.

To amplify signals obtained at DNA-modified electrodes in the presence of $Ru(NH_3)_6^{3+}$, we introduced an oxidant, $Fe(CN)_6^{3-}$, that would permit turnover of $Ru(NH_3)_6^{3+}$ by regenerating the oxidized form (FIG. 4). As shown in FIG. 5, large, irreversible reductive waves are observed at DNA-modified electrodes immersed in solutions of $Fe(CN)_6^{3-}$ and $Ru(NH_3)_6^{3+}$, consistent with the proposed reaction cycle (FIG. 5). The electrochemical signals obtained with DNA-modified electrodes from solutions of Ru(III) and Fe(III) are amplified by ~100-fold over those obtained when only $Ru(NH_3)_6^{3+}$ is present (no signal is obtained in this region when only $Fe(CN)_6^{3-}$ is present). The electrocatalysis requires DNA to attract the cation to the gold surface, as no signal is observed with a bare electrode.

This assay sensitively reports the presence of a target DNA sequence. The Ru(III)/Fe(III) signal monitored at a gold electrode modified with a probe sequence complementary to a portion of the *H. pylori* 23S rRNA gene (sequence: 5'-GGC AAG ACG GAA AGA CCC-3' (SEQ ID NO: 2)) significantly increases after exposure of the electrode to a synthetic target oligonucleotide (FIG. 5). The change in the electrochemical response is barely detectable in the absence of Fe(III). Short hybridization times (<1 hour) under mild conditions (40° C.) are sufficient to observe an increase in the electrocatalytic signal of >100%. In the presence of noncomplementary sequences or buffer lacking any DNA, no appreciable signal differences are observed.

The Ru(III)/Fe(III) electrocatalysis accurately reports hybridization of sequences of difference lengths and base composition. Both the 18-nt 23S rRNA sequence described above and a 30-nt sequence corresponding to a fragment of the Hpn gene (which encodes a protein unique to *H. pylori*, sequence: 5'-TGT TGC AGC ACT AGC GAT AGT CAT CAT CAA-3' (SEQ ID NO: 1)) can be detected as shown in FIG. 5A. It is also sensitive, as target concentrations down to 10 nM produced measurable increases in the electrochemical response after hybridization.

Example 4

Discrimination of Targets Containing Single-Base Substitutions

In experiments monitoring the hybridization of DNA oligonucleotides corresponding to a region of the *H. pylori* 23S rRNA, a pronounced sensitivity to mismatched base pairs within the target/probe complex was observed. The enhancement in the electrochemical signal typically observed with the WT rRNA sequence was significantly diminished when an A-to-C substitution at position 2143 within the 23S rRNA was introduced (sequence: 5'-GGC AAG ACG Gac AGA CCC-3' (SEQ ID NO: 3), the nucleotide corresponding to C2143 is in lower case). The A2143C variant is important because this substitution imparts resistance to clarithromycin, the antibiotic typically used to combat *H. pylori*, and about 10% of the infections observed clinically are clarithromycin resistant.

The discrimination of the A2143C mutant is a result of slower hybridization kinetics for the sequence that is mismatched with respect to the probe. A systematic study of the hybridization efficiency as a function of time for the WT versus A2143C target revealed that the extent of hybridization for the two sequences only becomes comparable with incubation times over 12 hours. The pronounced effect caused by the single-base mismatch within the target/probe complex is a significant finding. Previous studies of duplex hybridization in solution by other groups have characterized much more subtle effects, with association rates for two DNA oligonucleotides displaying little sensitivity to the loss of a single Watson-Crick pair, and dissociation rates that increase by about an order of magnitude in mismatched assemblies.[27] Therefore, it appears that heterogeneous hybridization reactions, with one oligonucleotide immobilized on an electrode surface, are much more sensitive to mismatches, a finding that provides the basis for distinguishing similar sequences with an electrochemical hybridization assay. The probe density that we use in our experiments also appears to amplify the effect, as studies using surface plasmon resonance to follow hybridization at gold surfaces with very low surface coverages have elucidated similar, but much less pronounced, effects.[22] A surface with a high coverage of negatively charged oligonucleotides may serve to further destabilize mismatched target/probe duplexes.

The electrocatalytic DNA detection assay described provides a sensitive and specific means to execute electrochemical genotyping. The method described will be useful for genetic analysis in a multiplexed format.

Example 5

Hpn Target Detection Using PCR Products, RNA Transcripts, and a Synthetic 30-mer Two probe sequences were tested with the different targets: HP2a (complementary Hpn probe) 5'-TTT TTT TTT TTT GAT GAC TAT CGC TAG TGC-3' (SEQ ID NO: 4) and HP2b (noncomplementary Hpn probe) 5'-TTT TTT TTT TTT GGG ATA ATT CTT CAC CGG-3' (SEQ ID NO: 5). The appended thymine bases allowed for the probe to be more accessible to the target. The complementary probe effectively detects the presence of the different target nucleic acids using the electrocatalytic Ru(III)/Fe(III) system.

The target sequences were as follows:

PCR (generated using asymmetric PCR as single-stranded DNA, portion complementary to probe is underlined):

5'-GGA GTC ATC ATG GCA CAC CAT GAA GAA CAG CAC GGC GGT CAT CAC CAC CAT CAC CAC CAC ACA CAC CAC CAC CAC TAT CAC GGC GGT GAA CAC CAC CAT CAC CAC CAC AGC TCT CAT CAT GAA GAA GGT TGT TGC A GCACTAGCGATAGTCATCATCAT CAA GAA GAG GGT TGC TGC CAC GGG CAT CAC GAG TAA TAT CGG TGT GGC TAG GGG CAA CTT-3' (SEQ ID NO: 6)

RNA (same sequence as PCR product, generated in vitro from DNA template, portion complementary to probe is underlined):

5'ATC AAA GGA GTC ATC ATG GCA CAC CAT GAA GAA CAG CAC GGC GGT CAT CAC CAC CAT CAC CAC CAC ACA CAC CAC CAC CAC CAC TAT CAC GGC GGT GAA CAC CAC CAT CAC CAC CAC AGC TCT CAT CAT GAA GAA GGT TGT TGC A GCACTAGCGATAGTCATCAT CAT CAA GAA GAG GGT TGC TGC CAC GGG CAT CAC GAG TAA TAT CGG TGT GGC TAG GGG CAA CTT-3' (SEQ ID NO: 7)

30-mer synthetic oligo

5'-TGT TGC AGCACTAGCGATAGTCATCATC AT CAA-3' (SEQ ID NO: 8)

DNA probe solutions (HP2a and HP2b) containing 5 μM ssDNA, 500 nM MCH, 50 mM $MgCl_2$, and 25 mM sodium phosphate/NaCl buffer pH 7 were deposited for 1.5 hours at room temperature in humidity chamber. Target solution containing synthetic 30-mer and PCR product contained 500 nM target, 100 mM $MgCl_2$, and 25 mM sodium phosphate/ NaCl buffer pH 7 and were exposed to DNA films for 1 hour at 45° C. RNA target hybridization was under the same conditions except 1 μM target was used.

Figure 7:
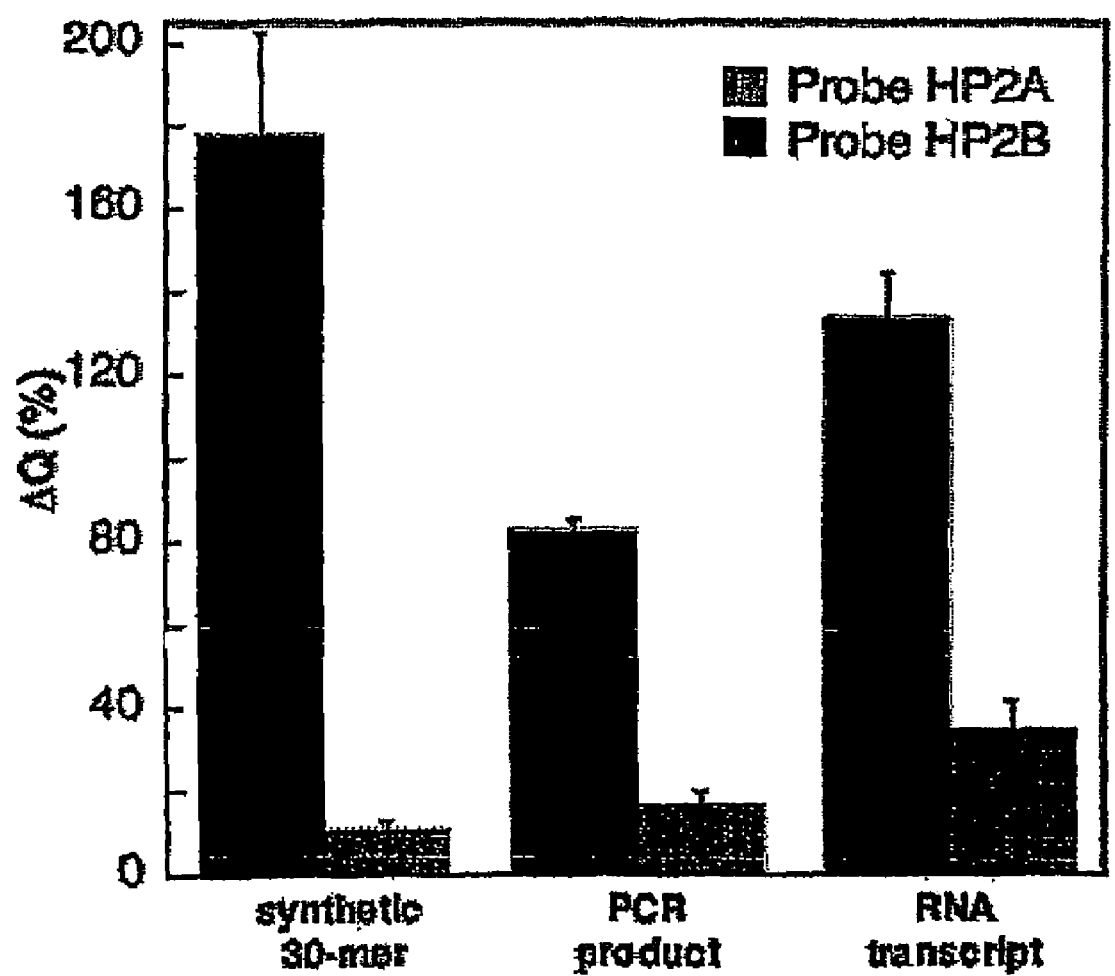
FIG. 7 is a bar graph showing the time dependence of hybridization for HP2A probe (complementary Hpn probe) and HP2B probe (noncomplementary Hpn probe).

The results are shown in FIG. 7, which is a bar graph showing the time dependence of hybridization for HP2A probe (complementary Hpn probe) and HP2B probe (non-complementary Hpn probe). It shows that target DNA sequences can be detected as either PCR products or RNA transcripts using the methods described herein.

Example 6

Preparation of Asymmetric PCR Amplicon and RNA Targets

The *H. pylori* hpn gene was PCR amplified from a recombinant source (an *E. coli* plasmid provided by Dr. Andrew Plaut of Tufts University). Two PCR products were generated, one using the asymmetric method that produces mainly single-stranded DNA, and another using conventional PCR conditions that would generate a double-stranded product for T7 runoff transcription of RNA. For the former reaction, a forward PCR primer (5'-ATC AAA GGA GTC ATC ATG GCA CAC-3' (SEQ ID NO: 9)) and reverse PCR primer (5'-AAG TTG CCC CTA GCC ACA-3' (SEQ ID NO: 10)) were used in reactions containing 1 μg/ml of plasmid DNA, 500 nM forward primer, 5 nM reverse primer, 1× of cloned Pfu DNA polymerase reaction buffer (200 mM Tris-HCl (pH 8.8), 100 mM KCl, 100 mM $(NH_4)2SO4$, 20 mM $MgSO_4$, 1% Triton X-100, 1 mg/ml nuclease-free bovine serum albumin), 1 mM dNTPs, and 2.5 U of cloned Pfu DNA polymerase, polymerase buffer and enzyme purchased from Stratagene, in a total reaction volume of 100 μL. For the synthesis of the PCR product used for the generation of the RNA transcript, a forward PCR primer containing the T7 polymerase promoter sequence (5'-GCT AGG TAA TAC GAC TCA CTA TAG GAG TCA TCA TGG CAC AC-3' (SEQ ID NO: 11)) was used with the same reaction conditions with the exception of the addition of 500 nM forward and 500 nM reverse primer. PCR was performed on a Stratagene Robocycler with 30 cycles at 94° C. for 2 minutes, 52° C. for 2 minutes, 72° C. for 3 minutes. PCR products were subjected to phenol-chloroform extraction and ethanol precipitation. RNA target was transcribed from amplified DNA template with T7 promoter region using standard conditions. The resultant DNA and RNA targets had the following sequences:

5'GGAGTCATCATGGCACACCATGAAGAACAGCA-CGGCGGTCATCACCACCATCACCACCACACACAC-

CACCACCACTATCACGGCGGTGAACACCACCATC-
ACCACCACAGCTCTCATCATGAAGAAGGTTGTTG-
CAGCACTAGCGATAGTCATCATCATCAAGAAGAG-
GGTTGCTGCCACGGGCATCACGAGTAATATCGGT-
GTGGCTAGGGGCAACTT3' (RNA, 219 nt) (SEQ ID NO: 6) and 5'ATCAAAGGAGTCATCATGGCACACCAT-
GAAGAACAGCACGGCGGTCATCACCACC ATCAC-
CACCACACACACCACCACCACTATCACG-
GCGGTGAACACCACCATCACCAC
CACAGCTCTCATCATGAAGAAGGTTGTTGCA
GCACTAGCGATAGTCATCATCATCAA GAAGAGGGT-
TGCTGCCACGGGCATCACGAG-
TAATATCGGTGTGGCTAGGGGCAACT T3' (DNA, 225 nt) (SEQ ID NO: 7); the portion of the sequence that is complementary to the HP1b probe is underlined.

Example 7

Electrocatalytic Reduction of $Ru(NH_3)_6^{3+}$ at DNA-Modified Surfaces $Ru(NH_3)_6^{3+}$, lacking any ligands that can bind to DNA intercalatively, associates electrostatically with the negatively charged backbone. It is therefore a sequence-neutral binder and an ideal probe for the quantitation of single- or double-stranded DNA adsorbed on an electrode surface. However, the limited concentration of $Ru(NH_3)_6^{3+}$ localized at DNA-modified electrodes yields a small current under conditions suitable for hybridization detection (i.e. concentrations of Ru(III) sufficiently low to prohibit direct adsorption of the redox-active probe). To provide maximal sensitivity for the detection of DNA hybridization, we introduced an oxidant, $Fe(CN)_6^{3-}$, that would permit turnover of $Ru(NH_3)_6^{3+}$ by regenerating the oxidized form (Scheme 1), thereby significantly amplifying the response obtained.

Figure 8:
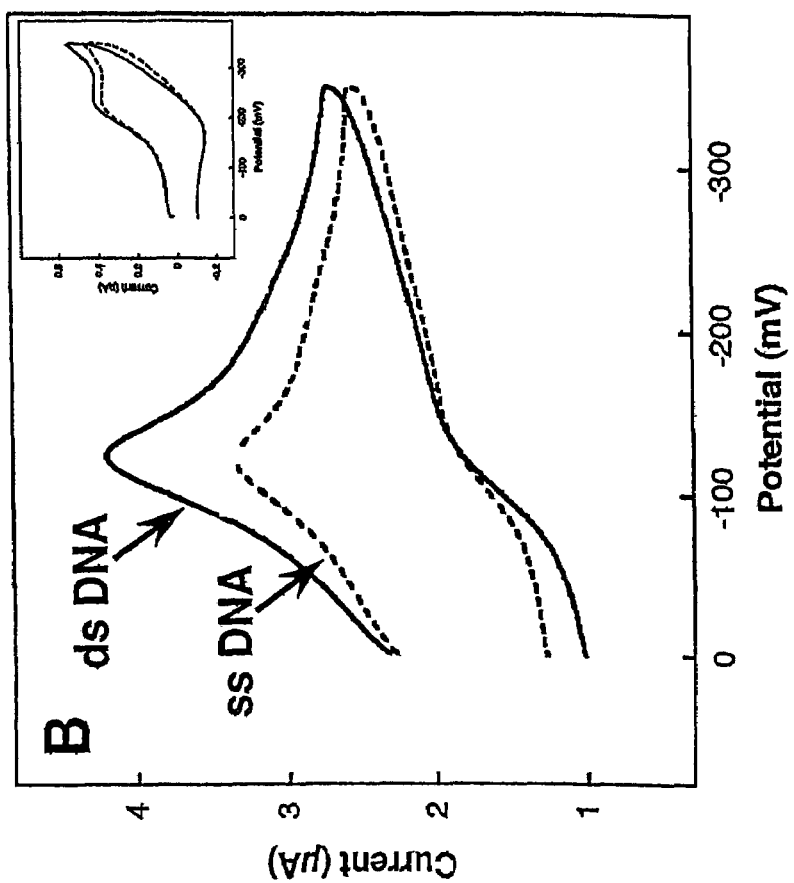
FIG. 8 is Ru(III)/Fe(III) electrocatalysis as a reporter of surface-immobilized DNA. (A) Dependence of electrocatalysis on DNA surface coverage. DNA films with varying densities were prepared by varying $MgCl_2$ concentration during exposure of gold substrates to probe solutions. Cyclic voltammograms obtained at electrodes modified in the presence of 10 (dotted line), 30 (dashed line), and 100 (solid line) mM $MgCl_2$ are shown. (B) Cyclic voltammograms illustrating enhancement of electrocatalytic signal upon hybridization of T2a (dotted line corresponds to CV obtained pre-hybridization, solid line corresponds to CV obtained after hybridization). DNA films were prepared in the presence of 50 mM $MgCl_2$. Hybridization with T2a was induced by introducing a solution containing 20 µM DNA, 25 mM sodium phosphate (pH 7), 25 mM NaCl, and 100 mM $MgCl_2$ for 30 minutes. The solution of target was heated to 40° C., deposited on an inverted electrode, and incubated for 30 minutes. No change in signal was obtained when buffer or a noncomplementary sequence (T-NC) was introduced. For comparison, voltammograms of a solution of 27 µM $Ru(NH_3)_6^{3+}$ obtained before (dotted line) and after hybridization (solid line) are shown.
Figure 8:
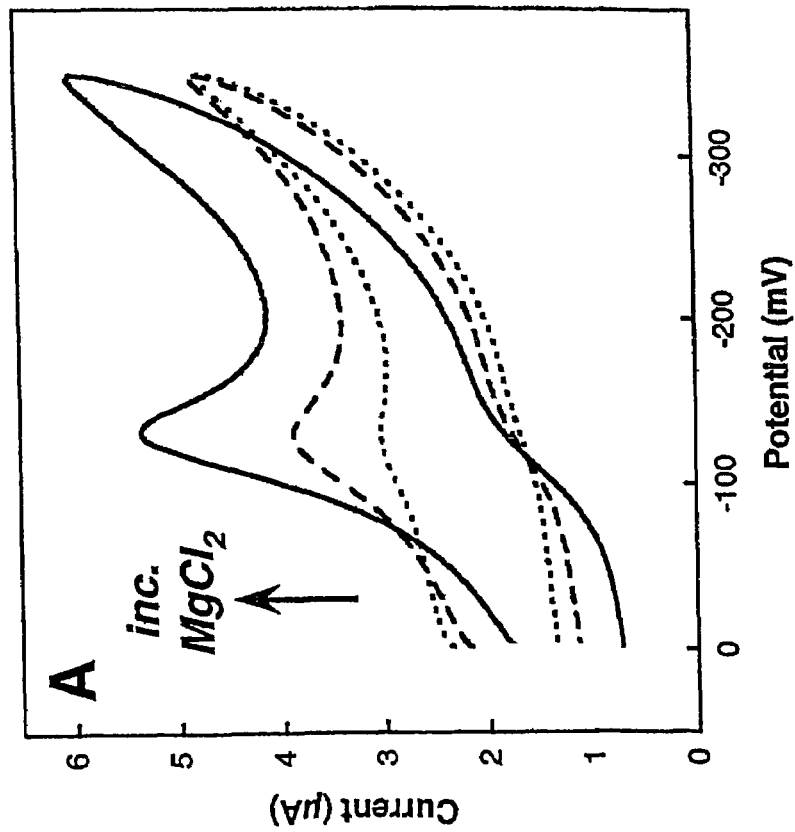

Indeed, as shown in FIG. 8, large, irreversible reductive waves are observed using cyclic voltammetry (CV) at DNA-modified electrodes immersed in solutions of $Fe(CN)_6^{3-}$ and $Ru(NH_3)_6^{3+}$, consistent with the proposed reaction. The amount of current observed reports the quantity of DNA present at the electrode surface, as the response obtained at surfaces featuring different densities (controlled by varying $[Mg^{2+}]$ during deposition) was directly dependent on the number of DNA molecules immobilized.

The electrochemical signals obtained with DNA-modified electrodes from solutions of Ru(III) and Fe(III) are amplified by ~100-fold over those obtained when only $Ru(NH_3)_6^{3+}$ is present (FIG. 8B inset); no signal is obtained in this region when only $Fe(CN)_6^{3-}$ is present (data not shown). The electrocatalysis requires DNA to attract the cationic complex to the gold surface, as no signal is observed with a bare electrode.

The electrocatalytic assay sensitively reports the presence of a complementary target DNA sequence. The $Ru(NH_3)_6^{3+}/Fe(CN)_6^{3-}$ signal monitored at a gold electrode modified with a probe sequence complementary to a portion of the *H. pylori* 23S rRNA gene (nucleotides 2132-2149) significantly increases after exposure of the electrode to a synthetic target oligonucleotide (FIG. 8B). Short hybridization times (<1 hour) and mild conditions are sufficient to observe an increase in the integrated charge of >100%. In the presence of noncomplementary sequences or buffer lacking any DNA, no appreciable signal differences are observed.

Figure 9:
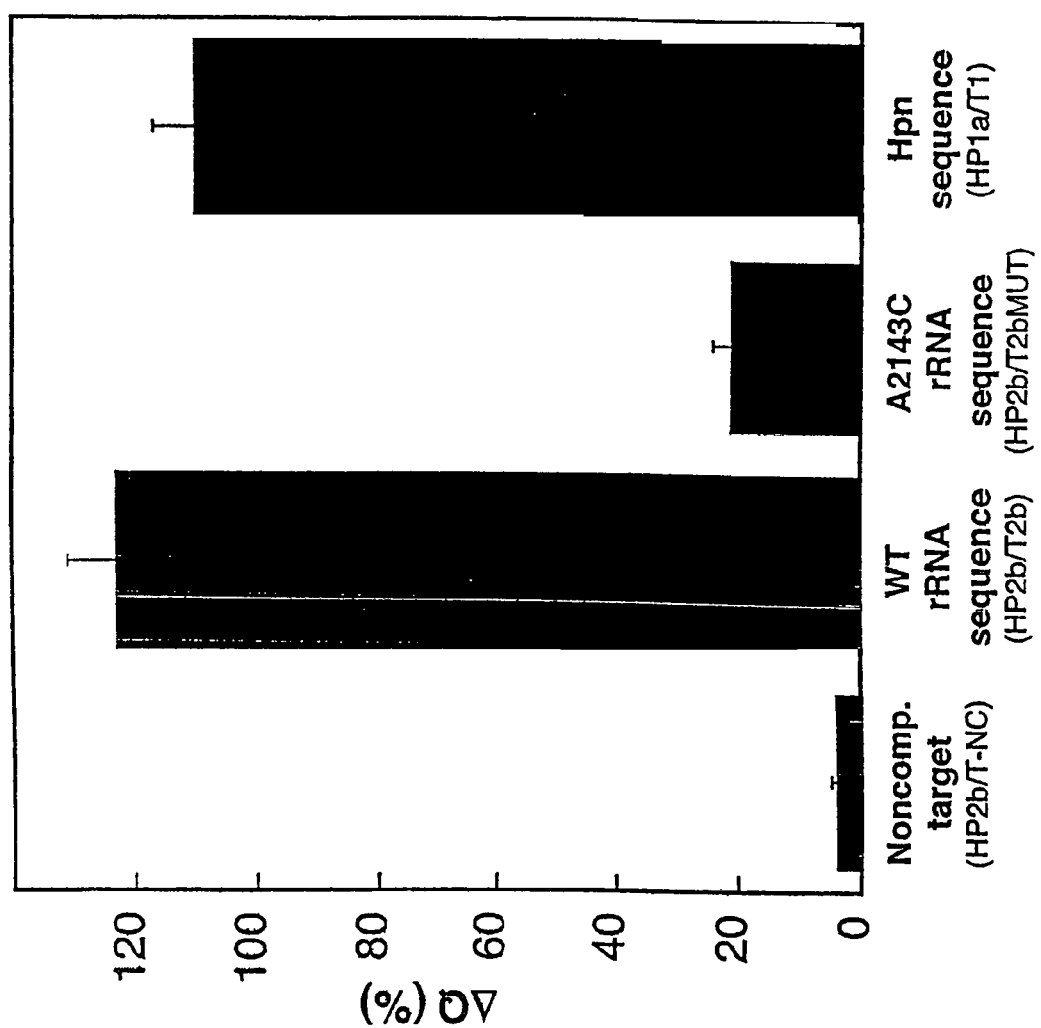
FIG. 9 shows detection of *H. pylori*-related sequences through changes in integrated charge obtained using electrocatalysis. Cyclic voltammetry was used to quantitate charge at electrodes exposed to different target/probe sequence pairs. Films of DNA probe sequences (HP2b and HP1a) were prepared as described in FIG. 8 with the exception that the 30-nucleotide probe sequence (HP1a) was deposited for 1.5 hours. The average integrated charge measured at probe-modified electrodes prior to hybridization is shown as a dotted line. Hybridization of all target sequences was allowed to proceed for 30 minutes and was otherwise performed as described in FIG. 8 with the exception of the inclusion of 200 mM $MgCl_2$ in the hybridization solution for the hpn target (T1).

The Ru(III)/Fe(III) electrocatalysis accurately reports hybridization of sequences of different lengths. Both the 18 nucleotide 23S rRNA sequence described above and a 30 nucleotide sequence corresponding to a fragment of the hpn gene (which encodes a histidine-rich protein of unknown function unique to *H. pylori*) can be detected as shown in FIG. 9. Thus, the assay described is versatile and is compatible with different probe sequence lengths and base composition. It is unnecessary to match the length of the target and probe, as experiments where the size of the target was increased by 10-15 nucleotides also produced successful hybridization detection (data not shown). The electrocatalytic assay is also sensitive, as target concentrations down to 10 nM (50 fmol) produced measurable increases in the electrochemical response after hybridization.

Example 8

Effect of Immobilized Probe Density

Figure 10:
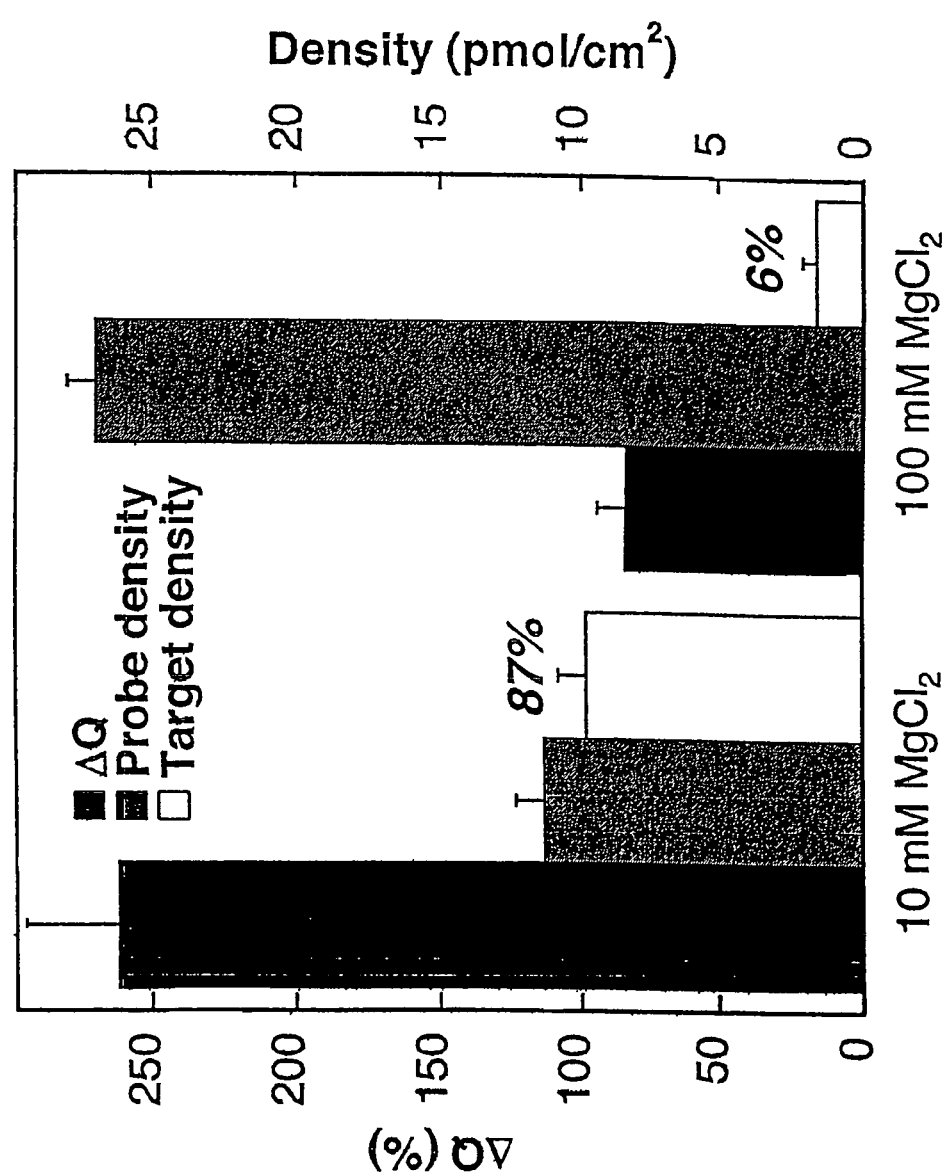
FIG. 10 shows dependence of hybridization efficiency on surface coverage. Fluorescein-modified thiolated probes and target sequences were used to quantitate absolute surface coverages, and cyclic voltammetry was used to quantitate changes in charge upon hybridization. The probe (HP2a) and target sequences (T2a) and experimental conditions are identical to FIG. 8A.

The efficiency of hybridization, investigated using the electrocatalytic assay and fluorescence-based quantitation, was sensitive to the density of the immobilized probe sequence (FIG. 10). As described above, the density of DNA films prepared with different amounts of $MgCl_2$ present was monitored using fluorescein-modified oligonucleotides. As the amount of $Mg^{2+}$ in the deposition solution increases, the density of probe increases, with films with 11 pmol DNA/$cm^2$ obtained with 10 mM $MgCl_2$ and films with 27 pmol DNA/$cm^2$ obtained with 100 mM $MgCl_2$. The response obtained in the presence of $Ru(NH_3)_6^{3+}$ and $Fe(CN)_6^{3-}$ was also monitored, and increased with the surface coverage. With the film prepared with 10 mM $MgCl_2$, the average charge measured was 0.13(5) µC, while with 100 mM $MgCl_2$ present during probe deposition, the average charge measured was 0.59(5) µC. The correlation between these values and the density of probe DNA indicates that the electrochemical signal exhibits a direct dependence on the concentration of immobilized DNA present at the electrode surface.

When signal increases upon hybridization were monitored for the electrodes with different surface coverages, it was observed that films with lower probe densities permitted more efficient target capture (FIG. 10). This effect has been observed in several studies and is proposed to arise because of steric crowding when local concentrations of immobilized DNA are high. While the lowest density film studied here (formed with 10 mM $MgCl_2$) allowed 87(±5)% hybridization, the highest density film (formed with 100 mM $MgCl_2$) displayed a much lower level of hybridization with 6(±2)% efficiency. The films prepared with 50 mM $MgCl_2$ that were routinely used in the electrocatalysis assay also displayed only partial hybridization, with 7(±2)% of probes forming a complex with a target DNA sequence. It is noteworthy, however, that the electrocatalytic assay was able to resolve this low level of target complexation with a change in the integrated charge of typically >100%.

Based on the dimensions of duplex DNA, ~50 pmol/$cm^2$ is the maximal coverage of duplexes that can be achieved. Therefore, it is apparent that the coverage of single-stranded probe must be well below this level to achieve efficient hybridization.

Example 9

Detecting Targets Containing Single-Base Substitutions

In experiments monitoring the hybridization of DNA oligonucleotides corresponding to a region of the *H. pylori*

23S rRNA, a pronounced sensitivity to mismatched base pairs within the target/probe complex was observed. The enhancement in the electrochemical signal typically observed with the WT rRNA sequence was significantly diminished when a sequence containing an A-to-C substitution at position 2143 was introduced (FIG. 9). The A2143C sequence is medically significant because this substitution imparts resistance to clarithromycin, the antibiotic typically used to combat *H. pylori*. Over 10% of the infections observed clinically are clarithromycin resistant.

Based on the thermal stabilities of the rRNA sequences used for these experiments, the observation of differential hybridization is surprising. The target/probe duplexes formed from the ribosomal sequences employed for this study exhibited $T_m$ values of 58(2)° C. when fully matched, and 52(2)° C. when the A2143C mutation was present that produced a C-T mismatch. Thus, it is reasonable to expect that both duplexes should be formed at the surface if the complexation was governed by thermodynamic stability.

Figure 11:
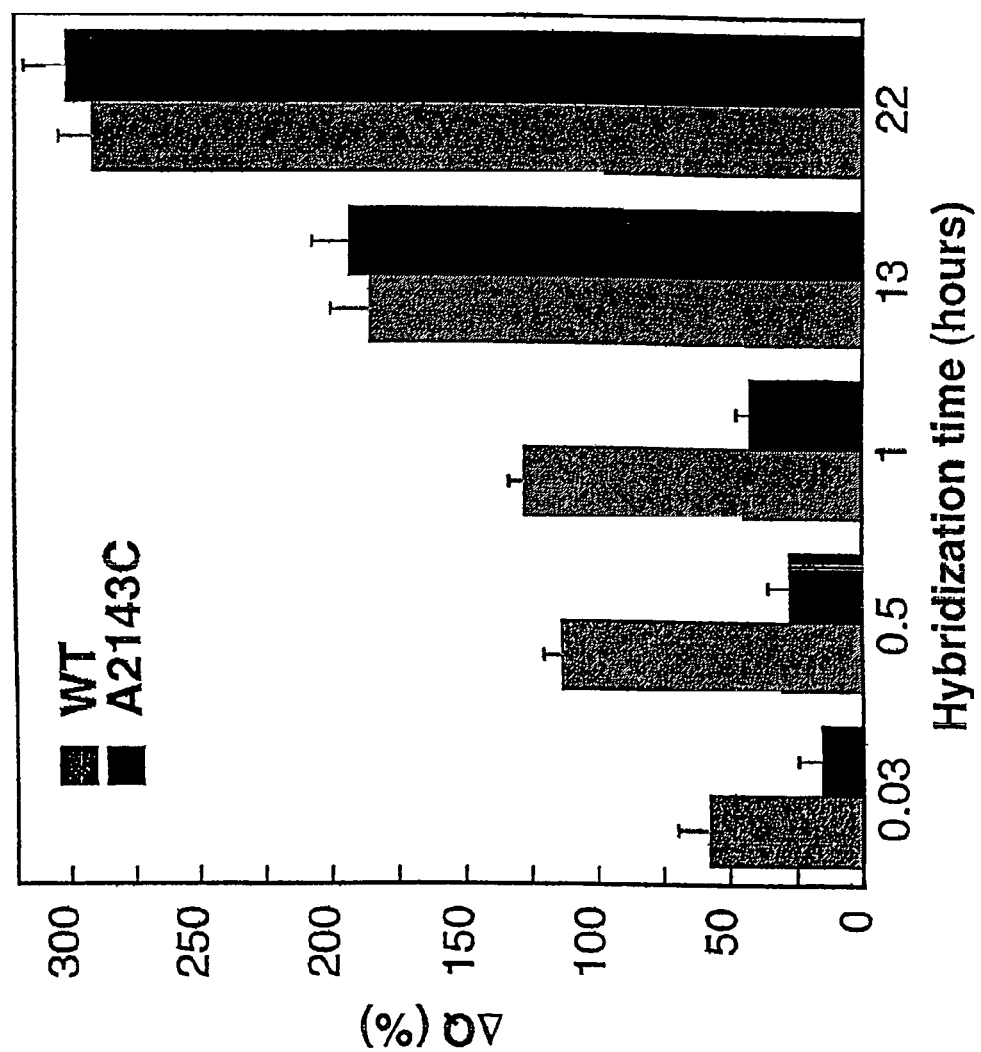
FIG. 11 shows time dependence of hybridization for WT and A2143C sequences corresponding to a fragment of the *H. pylori* 23S rRNA. Films of probe (HP2a) DNA were deposited from solutions containing 1 µM MCH, 5 µM ssDNA, and 0.8 M sodium phosphate (pH 7) for 1 hour at room temperature. Hybridization was performed with 1 µM target in 25 mM sodium phosphate (pH 7), 25 mM NaCl, and 100 mM $MgCl_2$ for the designated time. Electrodes were incubated at 40° C. during hybridization.

To investigate the origin of the differential hybridization observed in the presence of the point mutation, the time dependence of the hybridization was monitored (FIG. 11). With short incubation times, a pronounced difference in the signal obtained for the WT sequence was observed relative to the A2143C sequence. However, if the hybridization was permitted to proceed longer than 12 hours, comparable results were obtained with both sequences. Therefore, the discrimination of the A2143C mutation is a result of slower hybridization kinetics for the sequence that is mismatched with respect to the probe. The rate of association for both sequences is likely similar, thus the observed change may reflect a faster dissociation rate for the mismatched complex that limits the accumulation of hybridized duplexes.

Example 10

Detection of Extended DNA and RNA Targets

Figure 12:
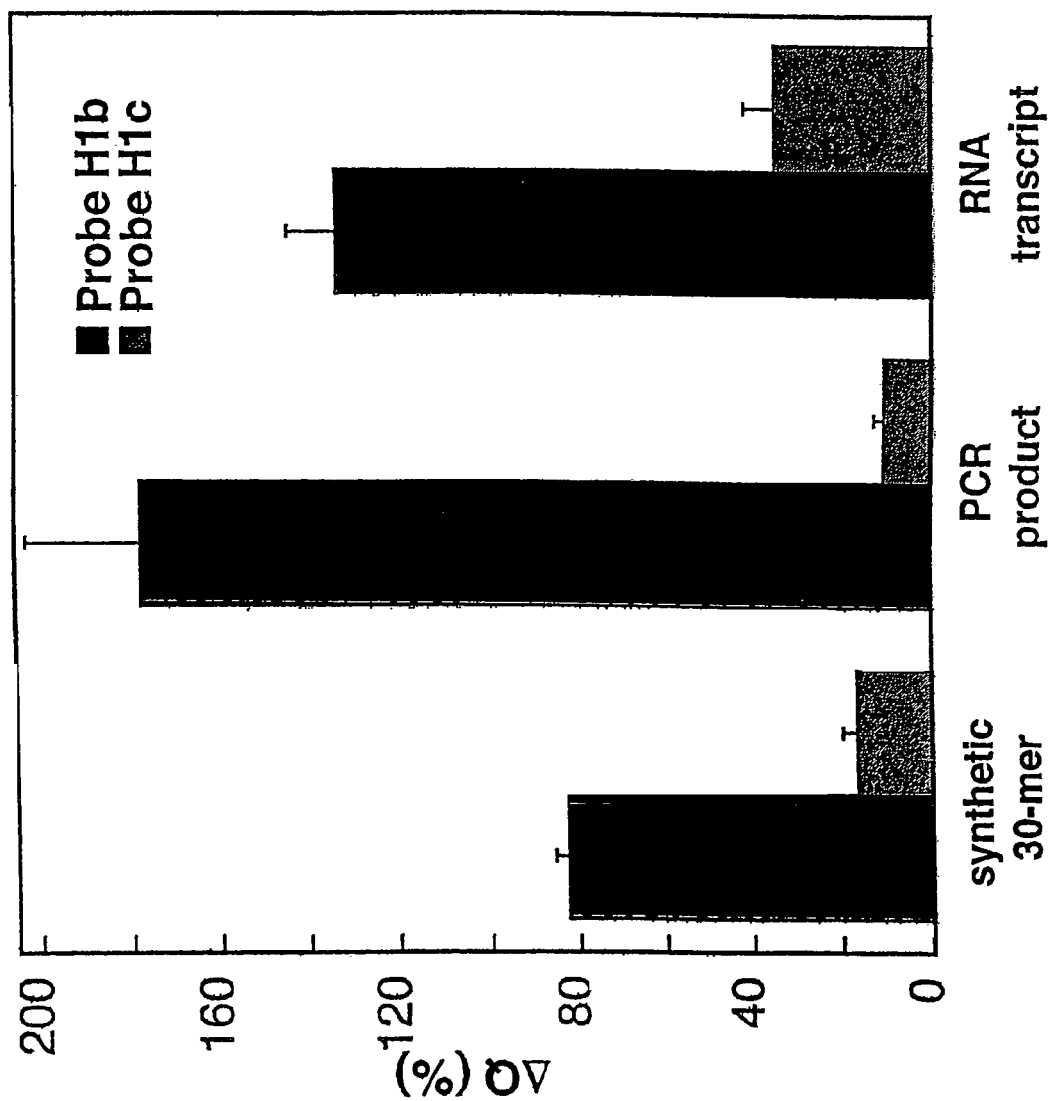
FIG. 12 shows electrocatalytic detection of extended DNA and RNA targets. DNA probe solutions (HP1b and HP1c) were deposited for 1.5 hours. Target solution containing synthetic 30-mer and PCR product contained 500 nM target, 100 mM $MgCl_2$, 25 mM sodium phosphate (pH 7), and 25 mM NaCl and were exposed to DNA films for 1 hour at 45° C. RNA target hybridization was under the same conditions except 1 µM RNA was used.

The applicability of the electrocatalytic assay to the detection of large DNA and RNA targets was tested using a >200 nucleotide sequence containing the *H. pylori* hpn gene (FIG. 12). For these hybridization experiments, probe sequences were employed containing a linker of 12 thymine residues that served to increase the accessibility of the portion of the oligonucleotide used for target capture. Using mild hybridization conditions (1 hour, 45° C.), single-stranded DNA made by asymmetric PCR and RNA generated in vitro was specifically detected via large increases in electrocatalytic currents obtained in the presence of a complementary probe. Low levels of non-specific binding were observed with a noncomplementary probe sequence, indicating that the increases in signal observed with the complementary probe resulted from the highly specific hybridization of the targets. It is noteworthy, however, that the RNA target reproducibly exhibited higher levels of nonspecific binding.

The electrocatalytic assay described here provides a sensitive means to detect nucleic acid sequences belonging to infectious pathogens with high specificity using electrochemical readout. The method is very sensitive, and is suitable for the detection of low levels of DNA hybridization from dilute solutions of target sequences. A particularly attractive feature of the method is the large signal enhancements that result from formation of duplex DNA on the electrode surface. Typically, the changes in integrated charge observed are greater than 100% even though the extent of hybridization at the electrode surface can be as low as 5-10%. Moreover, the unexpected finding that a single point mutation drastically attenuates the kinetics of duplex formation at the electrode surface indicates that hybridization-based bacterial genotyping is feasible, and that high-resolution sequence discrimination can be achieved with immobilized DNA probes. The further development of electrochemical tools such as the assay reported here that can be adapted for high-throughput analysis of DNA will enable efficient analysis of bacterial and human genes.

REFERENCES

1. M. M. Shi, "Technologies for individual genotyping: detection of genetic polymorphisms in drug targets and disease genes". *Am. J. Pharmacogenomics* 2002, 2, 197-205.
2. W. Vercoutere, and M. Akeson, "Biosensors for DNA sequence detection". *Curr. Opin. Chem. Biol.* 2002, 6, 816-822.
3. B. P. Nelson, M. R. Liles, K. B. Frederick, R. M. Corn, and R. M. Goodman, "Label-free detection of 16S ribosomal RNA hybridization on reusable DNA arrays using surface plasmon resonance imaging". *Environ. Microbiol.* 2002, 4, 735-743.
4. B. P. Nelson, T. E. Grimsrud, M. R. Liles, R. M. Goodman, and R. M. Corn, "Surface plasmon resonance imaging measurements of DNA and RNA hybridization adsorption onto DNA microarrays". *Anal. Chem.* 2001, 73, 1-7.
5. E. M. Southern, "DNA microarrays. History and overview". *Methods Mol. Biol.* 2001, 170, 1-15.
6. J. Wang, "From DNA biosensors to gene chips". *Nucleic Acids Res.* 2000, 28, 3011-3016.
7. K. M. Millan, and S. R. Mikkelsen, "Sequence-selective biosensor for DNA based on electroactive hybridization indicator". *Anal. Chem.* 1993, 65, 2317-2323.
8. K. Hashimoto, K. Ito, and Y. Ishimori, "Sequence-specific gene detection with gold electrode modified with DNA probes and an electrochemically active dye." *Anal. Chem.* 1994, 66, 3830.
9. K. Hashimoto, K. Ito, and Y. Ishimori, "Novel DNA sensor for electrochemical gene detection." *Anal. Chem. Acta.* 1994, 286, 219.
10. X.-H. Xu, H. C. Yang, T. E. Mallouk, and A. J. Bard, "Immobilization of DNA on an Aluminum(III) Alkanebisphosphonate Thin Film with Electrogenerated Chemiluminescent Detection". *J. Am. Chem. Soc.* 1994, 116, 8386-8387.
11. S. Liu, M. Wang, P. He, and Y. Fang, "Voltammetric determination of sequence-specific DNA by electroactive intercolator on graphite electrode". *Anal. Chim. Acta* 1996, 335, 239-243.
12. C. A. Mirkin, R. L. Letsinger, R. C. Mucic, and J. J. Storhoff, "A DNA-based method for rationally assembling nanoparticles into macroscopic materials". *Nature* 1996, 382, 607-609.
13. M. E. Napier, C. R. Loomis, M. F. Sistare, J. Kim, A. E. Eckhardt, and H. H. Thorp, "Probing biomolecule recognition with electron transfer: electrochemical sensors for DNA hybridization". *Bioconj. Chem.* 1997, 8, 906-913.
14. S. O. Kelley, E. M. Boon, J. K. Barton, N. M. Jackson, and M. G. Hill, "Single-base mismatch detection based on charge transduction through DNA". *Nucl. Acids Res.* 1999, 27, 4830-4837.

15. P. A. Ropp, and H. H. Thorp, "Site-selective electron transfer from purines to electrocatalysts: voltammetric detection of a biologically relevant deletion in hybridized DNA duplexes". *Chem. Biol.* 1999, 6, 599-605.
16. E. M. Boon, D. M. Ceres, T. G. Drummond, M. G. Hill, and J. K. Barton, "Mutation detection by electrocatalysis at DNA-modified electrodes." *Nat. Biotech.* 2000, 18, 1096.
17. M. I. Pividori, A. Merkoci, and S. Alegret, "Electrochemical genosensor design: immobilization of oligonucleotides onto transducer surfaces and detection methods". *Biosens. Bioelect.* 2000, 15, 291-303.
18. T. A. Taton, C. A. Mirkin, and R. L. Letsinger, "Scanometric DNA array detection with nanoparticle probes". *Science* 2000, 289, 1757-1760.
19. R. J. Heaton, A. W. Peterson, and R. M. Georgiadis, "Electrostatic surface plasmon resonance: direct electric field-induced hybridization and denaturation in monolayer nucleic acid films and label-free discrimination of base mismatches". *Proc. Natl. Acad. Sci. U.S.A.* 2001, 98, 3701-3704.
20. A. W. Peterson, R. J. Heaton, and R. M. Georgiadis, "The effect of surface probe density on DNA hybridization". *Nucl. Acids Res.* 2001, 29, 5163-5168.
21. P. M. Armistead, and H. H. Thorp, "Electrochemical detection of gene expression in tumor samples: overexpression of Rak nuclear tyrosine kinase". *Bioconj. Chem.* 2002, 13, 172-176.
22. A. W. Peterson, L. K. Wolf, and R. M. Georgiadis, "Hybridization of mismatched or partially matched DNA at surfaces". *J. Am. Chem. Soc.* 2002, 124, 14601-14607.
23. E. Palecek, M. Fojta, M. Tomschik, and J. Wang, "Electrochemical biosensors for DNA hybridization and DNA damage". *Biosens. Bioelectron.* 1998, 13, 621-628.
24. H. H. Thorp, "Cutting out the middleman: DNA biosensors based on electrochemical oxidation." *Trends in Biotechnology* 1998, 16, 117-121.
25. B. J. Taft, M. M. O'Keefe, J. T. Fourkas, and S. O. Kelley, "Engineering DNA-electrode connectivities: effect of linker length and structure". *Anal. Chim. Acta* 2003, in press.
26. A. B. Steel, T. M. Heme, and M. J. Tarlov, "Electrochemical quantitation of DNA immobilized on gold". *Anal. Chem.* 1998, 70, 4670-4677.
27. S. Wang, A. E. Friedman, and E. T. Kool, "Origins of high sequence selectivity: a stopped-flow kinetics study of DNA/RNA hybridization by duplex- and triplex-forming oligonucleotides". *Biochemistry* 1995, 34, 9774-9784.

All patents, patent applications, and published references cited herein are hereby incorporated by reference in their entirety. While this invention has been particularly shown and described with references to preferred embodiments thereof, it will be understood by those skilled in the art that various changes in form and details can be made therein without departing from the scope of the invention encompassed by the appended claims.

We claim:

1. An electrocatalytic hybridization assay comprising:
providing a nucleic acid probe engaged to a conductive solid support;
contacting the nucleic acid probe with a sample wherein the sample comprises a target nucleic acid, a first transition metal complex and a second transition metal complex;
and measuring an electrocatalytic signal generated by hybridization of the nucleic acid probe and the nucleic acid target, wherein the presence of the second transition metal complex provides an amplified electrocatalytic signal.

2. The electrocatalytic hybridization assay of claim 1 wherein the first transition metal complex comprises a metal selected from the group consisting of cobalt, iron, molybdenum, osmium, ruthenium and rhenium.

3. The electrocatalytic hybridization assay of claim 2 wherein the second transition metal complex comprises a metal selected from the group consisting of iron, cobalt, molybdenum, osmium and rhenium.

4. The electrocatalytic hybridization assay of claim 1 wherein the first transition metal complex is a transition metal ammonium complex.

5. The electrocatalytic hybridization assay of claim 4 wherein the second transition metal complex is a transition metal cynate complex.

6. The electrocatalytic hybridization assay of claim 1 wherein the solid support comprises gold.

7. The electrocatalytic hybridization assay of claim 1 further comprising comparing the measured electrocatalytic signal with a control.

8. A method of detecting hybridization between a nucleic acid probe and a target nucleic acid, comprising:
providing a nucleic acid probe engaged to a conductive solid support;
contacting the nucleic acid probe with a sample wherein the sample comprises a target nucleic acid, a first transition metal complex and a second transition metal complex; and
measuring an electrocatalytic signal generated by hybridization of the nucleic acid probe and the nucleic acid target.

9. The method of claim 8 further comprising: comparing the measured electrocatalytic signal with a control.

10. The method of claim 8 wherein the first transition metal complex comprises a metal selected from the group consisting of cobalt, iron, molybdenum, osmium, ruthenium and rhenium.

11. The method of claim 10 wherein the second transition metal complex comprises a metal selected from the group consisting of iron, cobalt, molybdenum, osmium and rhenium.

12. The method of claim 8 wherein the first transition metal complex is a transition metal ammonium complex.

13. The method of claim 12 wherein the second transition metal complex is a transition metal cynate complex.

14. The method of claim 8 wherein the conductive substrate comprises gold.

15. The method of claim 8 wherein the target nucleic acid is RNA.

16. A method of detecting hybridization between a nucleic acid probe and a target nucleic acid, comprising:
providing a nucleic acid probe engaged to a conductive solid support;
contacting the nucleic acid probe with a sample wherein the sample comprises a target nucleic acid, a first transition metal complex and a second transition metal complex wherein the first transition metal complex is a $Ru(NH_3)_6^{-3}$ complex and the second transition metal complex is a $Fe(CN)_6^{-3}$ complex; and
measuring an electrocatalytic signal generated by hybridization of the nucleic acid probe and the nucleic acid target.

17. The method of claim 16 further comprising: comparing the measured electrocatalytic signal with a control.

18. The method of claim 16 wherein the conductive substrate comprises gold.

19. The method of claim 16 wherein the target nucleic acid is RNA.

20. The method of claim 16 wherein the target nucleic acid is DNA.

* * * * *